US011382782B2

(12) United States Patent
Binmoeller et al.

(10) Patent No.: US 11,382,782 B2
(45) Date of Patent: *Jul. 12, 2022

(54) METHODS AND DEVICES TO CURB APPETITE AND/OR TO REDUCE FOOD INTAKE

(71) Applicant: Endosphere, Inc., Columbus, OH (US)

(72) Inventors: Kenneth F. Binmoeller, Rancho Santa Fe, CA (US); Matthew Yurek, San Diego, CA (US); Zhenyong Keck, Redwood City, CA (US); James T. McKinley, Redwood City, CA (US)

(73) Assignee: Endosphere, Inc., Columbus, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/225,682

(22) Filed: Aug. 1, 2016

(65) Prior Publication Data

US 2017/0181878 A1    Jun. 29, 2017

Related U.S. Application Data

(63) Continuation of application No. 14/062,744, filed on Oct. 24, 2013, now abandoned, which is a (Continued)

(51) Int. Cl.
*A61F 2/04* (2013.01)
*A61F 5/00* (2006.01)
*A61N 1/36* (2006.01)

(52) U.S. Cl.
CPC ........ *A61F 5/0076* (2013.01); *A61N 1/36007* (2013.01); *A61F 2002/044* (2013.01); *A61F 2002/045* (2013.01); *A61F 2210/0014* (2013.01)

(58) Field of Classification Search
CPC .. A61F 2002/045; A61F 5/0003; A61F 5/003; A61F 5/0013; A61F 5/0073; A61F 5/0076; A61F 5/0079
See application file for complete search history.

(56) References Cited

U.S. PATENT DOCUMENTS 4,315,509 A * 2/1982 Smit ..................... A61F 5/0076
                                                   417/474
4,607,618 A * 8/1986 Angelchik ............ A61F 5/0036
                                                   128/898

(Continued)

OTHER PUBLICATIONS

Definition of mesh from http://www.merriam-webster.com/dictionary/mesh retrieved Jan. 20, 2016. (Year: 2016).*

*Primary Examiner* — Megan Y Wolf
(74) *Attorney, Agent, or Firm* — Erickson Law Group, PC

(57) ABSTRACT

The present invention relates to devices and methods of operating the devices that contribute to curbing appetite and/or reducing food intake. In some embodiments, the methods and devices of the present invention include as intestinal/duodenal insert comprising an elongated member with at least one flow reduction element that can cause the stimulation of one or more biological signals of satiety. Some embodiments of the inserted device are anchored at the duodenal site by an anchoring member residing in the stomach, other embodiments of the device are stabilized at a targeted site by appropriate dimensions of length as well as one or more angled portions of the device that correspond to angled portions of the targeted site in the dodenum. Embodiments of the device exert effects by virtue of physical presence, as well as by more active forms of intervention, including release of bioactive materials and electrical stimulation of neurons.

14 Claims, 24 Drawing Sheets

Related U.S. Application Data continuation of application No. 11/807,107, filed on May 25, 2007, now Pat. No. 8,585,771, which is a continuation-in-part of application No. 11/300,283, filed on Dec. 15, 2005, now Pat. No. 8,147,561, which is a continuation-in-part of application No. 10/999,410, filed on Nov. 30, 2004, now Pat. No. 7,931,693.

(60) Provisional application No. 60/808,820, filed on May 26, 2006, provisional application No. 60/547,630, filed on Feb. 26, 2004.

(56) References Cited

U.S. PATENT DOCUMENTS

| | | | |
|---|---|---|---|
| 9,352,126 B2 * | 5/2016 | Binmoeller | A61M 25/04 |
| 2002/0183853 A1 * | 12/2002 | Mitchell | A61F 2/07 |
| | | | 623/23.7 |
| 2005/0033331 A1 * | 2/2005 | Burnett | A61B 5/14539 |
| | | | 606/154 |
| 2005/0267595 A1 * | 12/2005 | Chen | A61F 5/003 |
| | | | 623/23.65 |

\* cited by examiner

METHODS AND DEVICES TO CURB APPETITE AND/OR TO REDUCE FOOD INTAKE

CROSS REFERENCE TO RELATED APPLICATIONS

This application is a continuation of U.S. patent application Ser. No. 14/062,744, filed Oct. 24, 2013, titled "METHODS AND DEVICES TO CURB APPETITE AND/OR TO REDUCE FOOD INTAKE," now U.S. Patent Application Publication No. 2014-0114228-A1, which is a continuation of U.S. patent application Ser. No. 11/807,107, filed May 25, 2007, titled "METHODS AND DEVICES TO CURB APPETITE AND/OR TO REDUCE FOOD INTAKE," now U.S. Pat. No. 8,585,771, which claims priority to U.S. Provisional Patent Application No. 60/808,820, filed May 26, 2006, and titled "METHODS AND DEVICES TO CURB APPETITE AND/OR REDUCE FOOD INTAKE," each of which is herein incorporated by reference in its entirety.

U.S. patent application Ser. No. 11/807,107 is also a continuation-in-part of U.S. patent application Ser. No. 11/300,283, filed Dec. 15, 2005, titled "METHODS AND DEVICES TO CURB APPETITE AND/OR REDUCE FOOD INTAKE," now U.S. Pat. No. 8,147,561 which is a continuation-in-part of U.S. patent application Ser. No. 10/999,410, filed Nov. 30, 2004, titled "METHOD AND APPARATUS FOR REDUCING OBESITY," now U.S. Pat. No. 7,931,693 which claims priority to U.S. Provisional Patent Application No. 60/547,630, filed Feb. 26, 2004 and titled "ENDOSCOPIC MULTISPHERE ARRAY DEVICE," each of which is herein incorporated by reference in its entirety.

INCORPORATION BY REFERENCE

All publications and patent applications mentioned in this specification are herein incorporated by reference to the same extent as if each individual publication or patent application was specifically and individually indicated to be incorporated by reference.

FIELD

The invention is in the field of medical devices and methods related to curbing appetite and/or reducing food intake.

BACKGROUND

Obesity, defined as a body mass index (BMI) of greater than 30, is a major health concern in the United States and other countries; it has been estimated that one in three Americans and more than 300 million people world-wide are obese. Complications of obesity include many serious and life-threatening diseases including hypertension, diabetes, coronary artery disease, stroke, congestive heart failure, pulmonary insufficiency, multiple orthopedic problems, various cancers and a markedly decreased life expectancy. Intentional weight loss, however, can improve many of these medical complications associated with obesity.

While weight loss can improve many of the medical complications associated with obesity, its management as a health concern has proven troublesome. A variety of approaches including dietary methods, psychotherapy, behavior modification, and pharmacotherapy have each met with some success but as a whole failed to effectively control the rapid growth in the incidence and severity of obesity seen in the United States. The severity of problems associated with obesity also has led to the development of several drastic surgical procedures. One such procedure physically reduces the size of the stomach so that a person cannot consume as much food as was previously possible. These stomach reduction surgeries had limited early success, but now it is known that the stomach can stretch back to a larger volume over time, limiting the achievement of sustained weight loss in many individuals. Another drastic surgical procedure induces the malabsorption of food by reducing the absorptive surface of the gastrointestinal (GI) tract, generally via by-passing portions of the small intestine. This gastric by-pass procedure further has been combined with stomach reduction surgery. While these described surgical procedures can be effective to induce a reduction in food intake and/or overall weight loss in some, the surgical procedures are highly invasive and cause undue pain and discomfort. Further, the described procedures may result in numerous life-threatening postoperative complications. These surgical procedures are also expensive, difficult to reverse, and place a large burden on the national health care system.

Non-surgical approaches for the treatment of obesity also have been developed. For example, one non-surgical endoscopic approach to treating obesity includes the placement of a gastric balloon within the stomach. The gastric balloon fills a portion of the stomach, providing the patient with a feeling of fullness, thereby reducing food intake. This approach has yet to be convincingly shown to be successful, and a number of problems are associated with the gastric balloon device, however, including poor patient tolerance and complications due to rupture and/or migration of the balloon. Other non-surgical devices designed to induce weight loss limit the absorption of nutrients in the small intestine by funneling food from the stomach into a tube found within the small intestine so that the food is not fully digested or absorbed within the small intestine. While this type of device may be somewhat effective at limiting the absorption of consumed food, there is still room for a variety of improvements in non-surgical devices designed to induce weight loss and/or a reduction in food intake.

An understanding of biological events that contribute to the creation of satiety signals provides an opportunity to develop "smart" nonsurgical devices that can trigger such events. The amount of food that individuals consume is largely dependent on biological signals between the gut and the brain. Specifically, hormonal signals from the gut to the brain are correlated with both the onset and cessation of food intake. While increased levels of hormones such as ghrelin, motilin and agouti-related peptide are involved in the promotion of appetite and the onset of food intake, increased levels of a number of other hormones are involved in the cessation of food intake.

Various biologic events contribute to the physiologic cessation of food intake. Generally, as a meal is consumed, the ingested food and by-products of digestion interact with an array of receptors along the GI tract to create satiety signals. Satiety signals communicate to the brain that an adequate amount of food has been consumed and that an organism should stop eating. Specifically, GI tract chemoreceptors respond to products of digestion (such as sugars, fatty acids, amino acids and peptides) while stretch and mechanoreceptors in the stomach and proximal small intestine respond to the physical presence of consumed foods. Chemoreceptors respond to the products of digestion by causing the release of hormones or other molecular signals. These released hormones and/or other molecular signals can stimulate nerve fibers to send satiety signals to the brain. The arrival of these signals in the brain can trigger a variety of neural pathways that can reduce food intake. The released hormones and/or other molecular signals can also travel to the brain themselves to help create signals of satiety. Stretch and mechanoreceptors generally send satiety signals to the brain through stimulation of nerve fibers in the periphery that signal the brain. The present invention provides methods and devices that help to reduce food intake by providing non-surgical devices and methods that trigger the aforementioned biological events that contribute to the creation of satiety signals.

SUMMARY OF THE DISCLOSURE

The invention relates to a device to be inserted in the small intestine, which may be referred to generally as a small-intestinal insert. First to be summarized are embodiments that include a biodegradable material. Embodiments of the insert include an elongated or central member with a proximal end, a distal end, at least one angled portion between the proximal end and the distal end, the angled portion corresponding to at least one angled target site within the small intestine, and at least a portion of the insert formed of a biodegradable material. Embodiments may include an elongated member configured initially to sit stably within the targeted site, and then, following degradation of the biodegradable material, configured to destabilize such that it becomes unseated from the target site, and can then be eliminated from the body through the intestinal tract.

In some embodiments, the angled portion includes biodegradable material. In some embodiments, the angled portion includes a shape memory material. In some of these embodiments, the shape memory material includes any of a shape memory alloy or a biodegradable shape memory polymer. In other embodiments, the angled portion includes both a shape memory alloy portion and a biodegradable portion. In some of these latter embodiments, the biodegradable portion, upon degradation, is configured to facilitate the destabilization and elimination of the shape memory alloy portion. In some of these embodiments, the shape memory alloy portion and the biodegradable portion are joined at a junction, the junction being configured to degrade as the biodegradable portion degrades.

In some embodiments, the angled target site in the small intestine is in the duodenum. Further, in some embodiments, the angled target site in the duodenum includes two angles, and the insert has two angles corresponding to two angles of the duodenum.

In some embodiments of the small intestinal insert, the device includes at least one flow reduction element supported by the elongated member, the flow reduction element being configured to reduce the flow rate of chyme in the small intestine. In some of these embodiments, the flow reduction element is formed at least in part from a biodegradable material. In some embodiments, the flow reduction element includes any of a rib, a net, a sleeve, a basket, a centrally mounted baffle, a peripherally mounted baffle, a foam-like material, or a fan. In embodiments of the flow reduction elements that include a foam-like material, the foam-like material may include any of an open cell foam, a closed cell foam, or a hydrogel. In some of these embodiments, the foam-like material includes a bioactive material incorporated thereinto. And in some of these embodiments, the foam-like material is biodegradable, and the bioactive material is released upon degradation of the foam-like material. In other embodiments, the flow reduction element includes at least one releasable reservoir of one or more bioactive materials.

In some embodiments with flow reduction elements, the elements reduce the rate of the chyme flow sufficiently to alter its biochemical profile. And in some of these embodiments, the biochemical profile is altered sufficiently to cause the generation of a hormonal signal of satiety.

In some embodiments, the physical dimension of the insert is such the insert distends a portion of the small intestine when the insert is seated therein, and the distension is sufficient to cause stretch receptors or other neurons of the small intestine to generate a satiety signal in response thereto. The physical dimensions or features of the insert that cause distension include any of length, width, volume, density, weight, porosity, or surface properties.

Some embodiments of the insert include one or more releasable reservoirs containing one or more bioactive materials, the one or more reservoirs supported either directly or indirectly by the elongated member, and further include an active drug release mechanism also supported either directly or indirectly by the elongated member, the active drug release mechanism and the one or more releasable reservoirs being in operable communication with each other.

Some embodiments of the insert include a pump as a part of the active drug release mechanism for delivering a bioactive material, the pump being supported by the elongate member and coupled to the one or more releasable reservoirs. Embodiments of the pump may include any of an osmotic pump, an electrically-driven mechanical pump, a piezoelectric pump, a flow-driven pump, or a peristaltic-action driven pump. Some of these embodiments further include an energy storage element configured to provide energy to the pump. And in some of these embodiments, the pump is controlled by a remote device.

In other embodiments, the insert may further include an electronic emitter or neurostimulator configured to apply an electrical potential to a site in any of the small intestine or stomach, the emitter supported by the elongate member. In some of these embodiments, the the emitter, upon activation, stimulates a neuronal response that contributes to a signal of satiety. In some embodiments, the device further may include an energy storage element or apparatus configured to provide energy to the pump, and in some embodiments, the electronic emitter may be controlled by a remote device.

Some embodiments of the device may further include an anchoring member engaged to the proximal end of the elongated member, the anchoring member being configured to contribute to the stabilization of the device in the targeted site. In some of these anchored embodiments, the anchoring member resides in the stomach when the elongate member is seated in the target site within the small intestine.

Second to be summarized are embodiments of a small intestinal insert that include a neurological stimulator to electrically stimulate nerves in the small intestine, such nerves engaged in the generation of signals of satiety. This aspect of the invention relates to a small intestinal insert that includes an elongated member including a proximal end, a distal end, at least one angled portion between the proximal end and the distal end, the angled portion corresponding to at least one angled target site within the small intestine, wherein the at least one angled portion of the insert corresponds to at least one angled target site within the small intestine, and a neurological stimulator, supported by the elongate member.

In some of these embodiments, the insert includes a portion formed from a biodegradable material. Some of these embodiments are configured initially to sit stably within the targeted site, and then, following degradation of the biodegradable material, they are configured to destabilize such that it becomes unseated from the target site, and may be eliminated from the body by way of the intestinal tract.

In some embodiments, the neurological stimulator is adapted to stimulate one or more nerves of the small intestine sufficiently to generate one or more signals of satiety. In some of these embodiments, the insert further includes an energy storage element configured to provide energy to the neurological stimulator. And in some of these embodiments, the neurological stimulator is controlled by a remote device.

In some embodiments of the insert, the angled target site in the small intestine is in the duodenum. And in some embodiments the angled target site in the duodenum includes two angles, the insert having two angles corresponding to two angles of the duodenum.

In some embodiments, the insert includes at least one flow reduction element, the element configured to reduce the flow rate of chyme in the small intestine. And in some of these embodiments, the flow reduction element is formed at least in part from a biodegradable material.

In some embodiments of the insert, at least a portion of the insert is formed of a biodegradable material, the elongated member configured initially to sit stably within the targeted site, and then, following degradation of the biodegradable material, configured to destabilize such that it becomes unseated from the target site. In some of these embodiments, the angled portion of the insert includes biodegradable material. In still other embodiments, the insert may further include an anchoring member engaged to the proximal end of the elongated member, the anchoring member configured to contribute to the stabilization of the device in the targeted site.

Third to be summarized are embodiments of a small intestinal insert that include one or more releasable reservoirs containing one or more bioactive materials and an active drug release mechanism coupled to the reservoirs for conveying bioactive materials to the intraduodenal site. This aspect of the invention relates to a small intestinal insert that includes an elongated member including a proximal end, a distal end, at least one angled portion between the proximal end and the distal end, the angled portion corresponding to at least one angled target site within the small intestine, wherein the at least one angled portion of the insert corresponds to at least one angled target site within the small intestine, and one or more releasable reservoirs containing one or more bioactive materials, the one or more reservoirs supported by the elongated member; and an active drug release mechanism supported by the elongated member, the active drug release mechanism and the one or more releasable reservoirs in operable communication with each other.

In some of these embodiments, the insert includes a portion formed from a biodegradable material. Some of these embodiments are configured initially to sit stably within the targeted site, and then, following degradation of the biodegradable material, they are configured to destabilize such that it becomes unseated from the target site, and may be eliminated from the body by way of the intestinal tract. In some of these embodiments, it is the angled portion of the device that includes the biodegradable material.

Embodiments of the insert may include a drug release mechanism that may include any of an osmotic pump, an electrically-driven mechanical pump, a flow-driven pump, a peristaltic-action driven pump, or a piezoelectric pump. Embodiments may further include an energy storage element configured to provide energy to the pump. In some embodiments, the active drug release mechanism is controlled by a remote device. In some of these embodiments, the bioactive materials released by the active drug release mechanism are sufficient to generate a signal of satiety.

In some of these embodiments, the angled target site in the small intestine is in the duodenum. And in some of these embodiments, the angled target site in the duodenum comprises two angles, the insert having two angles corresponding to two angles of the duodenum.

In some embodiments of the insert, the angled portion comprises a shape memory portion. In other embodiments, the angled portion includes a shape memory alloy portion and a biodegradable portion. Some embodiments of the insert further include an electronic emitter configured to apply an electrical potential to a site in the small intestine, the site generating a neuronal response that contributes to a signal of satiety.

The invention further relates to methods of generating satiety in a subject by inserting an intraduodenal inserted device into a subject. The first methods to be summarized are those that use embodiments of the devise, as described above, which include a biodegradable material. Embodiments used in this method include an elongated member with a proximal end, a distal end, at least one angled portion between the proximal end and the distal end, the angled portion corresponding to at least one angled target site within the small intestine, and at least a portion of the insert formed of a biodegradable material, the elongated member configured initially to sit stably within the targeted site, and then, following degradation of the biodegradable material, configured to destabilize such that it becomes unseated from the target site. The method of using this device includes generating one or more signals of satiety due to one or more effects of any of the presence of the insert or by an active intervention by the insert.

The method may further include biodegrading the biodegradable material of the insert, unseating the devise from the target site, and eliminating it from the body. In some embodiments of the method, wherein the insert includes a portion with a shape memory alloy, biodegrading the biodegradable material facilitates elimination of the shape memory alloy portion.

In some embodiments of the method, where the insert further comprises chyme flow reduction elements, the method further includes slowing the passage of chyme with the flow reduction elements. In some of these embodiments, slowing the passage of chyme changes the biochemical profile of the chyme. And in some of these embodiments, changing the biochemical profile of the chyme activates cells in the intestine such as chemoreceptors, the chemoreceptors generating a neuronal signal or secreting a bioactive material in response thereto.

In some embodiments of the method, generating a satiety signal includes stretch-sensitive neurons of the intestine responding to distension of at least a portion of the duodenum due to the presence of the insert. In some embodiments of the method, generating a satiety signal includes cells of the intestine secreting one or more bioactive materials in response to the presence of the insert.

In some embodiments of the method, where the insert further comprises bioactive materials in releasable reservoirs, an active intervention by the insert includes the insert releasing one or more bioactive materials. In some of these embodiments, releasing one or more bioactive materials includes effluxing or eluting from the reservoir. In other embodiments, where the insert further includes a pump in operable connection with the releasable reservoirs, and releasing one or more bioactive materials includes pumping the materials from the reservoir. In such embodiments, the pumping may be from any of an osmotic pump, an electrically-driven pump, a piezoelectric structure, a flow-driven pump, or a peristalsis-driven pump.

In some embodiments, where the bioactive materials are included within a portion of the device comprising biodegradable materials, and the bioactive materials are released upon degradation of the biodegradable material. In some embodiments, the biodegradable materials are included in one or more flow reduction elements of the insert that include a foam-like material, such as an open cell foam, a closed cell foam, or a hydrogel.

In some embodiments where the insert further includes a neurological stimulator supported by the elongated member, the active intervention includes stimulating one or more nerves of the duodenum with the stimulator.

The invention further relates to methods, the second to be described, of generating satiety in a subject by positioning an embodiment of intraduodenal inserted device that includes a neurological stimulator into a subject. The insert embodiment includes an elongated member including a proximal end, a distal end, at least one angled portion between the proximal end and the distal end, the angled portion corresponding to at least one angled target site within the small intestine, and a neurological stimulator, supported by the elongated member; the method including stimulating nerves of the duodenum with the neurological stimulator. The method may include, more specifically, stretch-sensitive neurons of the intestine, which responding to the distending presence of the insert by sending a signal of satiety.

The method may further include slowing the passage of chyme with the flow reduction elements, such slowing of chyme flow contributing to further generation of satiety signals. The method may further include endocrine cells of the intestine responding to the neurological stimulator by any of direct or neurally-mediated pathways, the response including secreting one or more hormones.

Where the insert includes bioactive materials in releasable reservoirs, the method may further include the insert releasing one or more bioactive materials. In some embodiments, the insert includes biodegradable materials, and the method further includes biodegrading the biodegradable material of the insert and eliminating the insert from the body.

The invention further relates to a third set of methods of generating satiety in a subject by positioning an embodiment of intraduodenal inserted device that includes one or more releasable reservoirs containing one or more bioactive materials and an active drug release mechanism. The insert embodiment includes an elongated member including a proximal end, a distal end, at least one angled portion between the proximal end and the distal end, the angled portion corresponding to at least one angled target site within the small intestine, and one or more releasable reservoirs containing one or more bioactive materials, the one or more reservoirs supported by the elongated member; and an active drug release mechanism supported by the elongated member, the active drug release mechanism and the one or more releasable reservoirs in operable communication with each other. A method of using this embodiment includes releasing the one or more bioactive agents into the duodenum.

In some embodiments, releasing one or more bioactive materials includes pumping from the reservoir. Pumps included in the embodiment of the insert may include any of an osmotic pump, an electrically-driven pump, a piezoelectric structure, a flow-driven pump, or a peristalsis-driven pump.

Embodiments of the method may further include slowing the passage of chyme with the flow reduction elements, such slowing of chyme flow contributing to further generation of satiety signals. Embodiments of the method may further include stretch-sensitive neurons of the intestine responding to the physical presence of the insert. Embodiments of the method may still further include endocrine cells of the intestine secreting one or more hormones in response to any of the physical presence of the insert in response to the bioactive agents released by the active drug release mechanism. The embodiments of the method may still further include biodegrading the biodegradable material of the insert and eliminating the insert from the body.

BRIEF DESCRIPTION OF THE DRAWINGS

FIG. 30A shows the central member in an intact configuration; FIG. 30B shows the central member after biodegradation.

FIG. 31A shows the central member in an intact configuration; FIG. 31B shows the central member after biodegradation.

DETAILED DESCRIPTION

Embodiments of the Device In Situ

Figure 1:
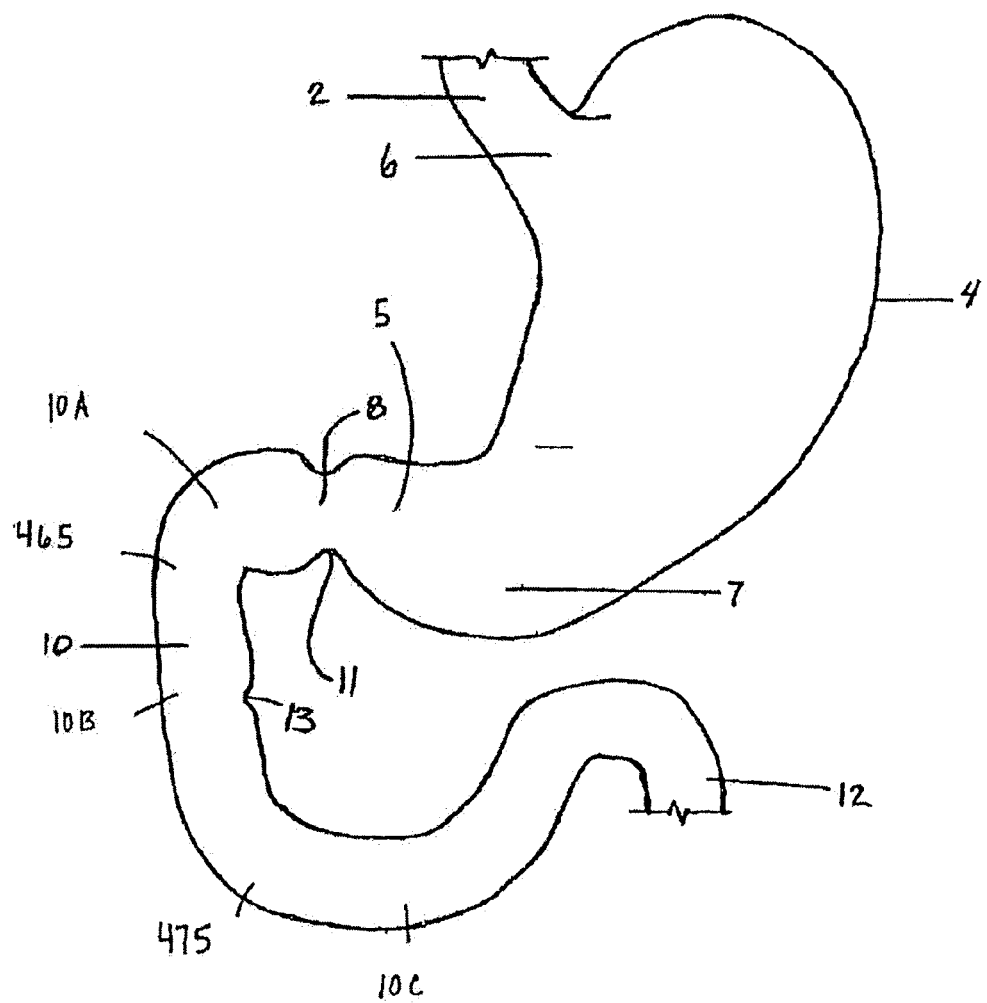
FIG. 1 is a general drawing of the stomach and duodenum of the small intestine.

FIG. 1 provides a view of the human gastrointestinal (GI) tract, including the stomach 4 and duodenum of the small intestine 10. Important features are the esophagus 2, stomach 4, antrum 7, pylorus 8, pyloric valve 11, duodenum 10, jejunum 12 and ampulla of Vater (or hepatopancreatic ampulla) 13, which is formed by the union of the pancreatic duct and the common bile duct. Functionally, the esophagus 2 begins at the nose or mouth at its superior end and ends at the stomach 4 at its inferior end. The stomach 4 encloses a chamber which is characterized, in part, by the esophageal-gastric juncture 6 (an opening for the esophagus 2) and the antrum-pyloric juncture 5 (a passageway between the antrum 7 through the pylorus 8 to the duodenum 10 of the small intestine). The pylorus 8 controls the discharge of contents of the stomach 4 through a sphincter muscle, the pyloric valve 11, which allows the pylorus 8 to open wide enough to pass sufficiently-digested stomach contents (i.e., objects of about one cubic centimeter or less). These gastric contents, after passing into the duodenum 10, continue into the jejunum 12 and on into the ileum (not shown). The duodenum 10, jejunum 12 and ileum make up what is known as the small intestine. However these individual portions of the alimentary canal are sometimes individually referred to as the small intestine. In the context of this invention the small intestine can refer to all or part of the duodenum, jejunum and/or ileum. The ampulla of Vater 13, which provides bile and pancreatic fluids that aid in digestion is shown as a small protrusion on the medial wall of the duodenum 10.

Embodiments of the inventive device include two basic forms. Some embodiments of the intestinal insert are stabilized in the intestine by way of an anchoring member that resides in the stomach and is too large to be swept through the pylorus. Other embodiments reside stably in the intestine not by virtue of a separate anchoring member in the stomach, but rather by virtue of the device as a whole fitting into the small intestine with angled portions that fit or correspond with angled portions of the intestine, and the device further having a sufficient structural integrity that it resists being moved distally because the distal location does not physically accommodate the shape of the device. Aspects of the device that are adapted to provide anchorless stabilization at a target site in the intestine include physical dimensions of length and width, as well as angles of the device, all of which complement the target portion of intestine. In other embodiments, stabilizing features in the intestine may include expanded portions of the device in the duodenal bulb, which is larger than the more distal portion of the duodenum, and which thereby effectively prevents distal movement (as in FIG. 18, for example). Other stabilizing or anchoring elements may include any of hooks, barbs, or protrusions on the device that engage the wall of the intestine.

Some embodiments of the device and associated methods of using the device are directed toward reducing the rate of food transit through the intestine by physical mechanisms of intervening in the rate of food transit. In other aspects, embodiments of the invention act by eliciting satiety signals by way of physiological mechanisms, or, alternatively, by directly providing satiety signals through bioactive materials or agents, or by neuronal stimulation, thereby reducing food intake behaviorally. Some embodiments of the device are directed toward medical purposes broader than satiety and digestive physiology alone, although the satiety and food consumption functionalities of embodiments of the device and method will be described herein in greater detail. In some aspects, embodiments of the device may contribute to slowing food transit and/or reducing food intake by the satiety signals generated by the intestine in direct response to the mere physical presence of the device. Such signals could, for example, be mediated by stretch-responsive neurons or mechanoreceptors in the intestinal wall. In other embodiments, satiety signals could be mediated by hormones that are responsive to physical presence of material in the intestine, or which are secondarily responsive to mechano-receptors. In other embodiments, the slowing of food or the increased residency time, and the consequent change in the chemical environment of the intestine, may elicit responses from chemoreceptors residing in the intestine to signal either neurally or hormonally in such a way that has a net effect of signaling satiety.

In still other embodiments of the invention, the device may convey bioactive material or agents that are released over time within the intestine, the bioactive agents conveying a net signal of satiety. In some embodiments, the bioactive agents with a net satiety signaling effect are passively released from sites such as coatings, depots, or reservoirs within the device. Bioactive materials or agents have been described in detail above, but briefly and in broad aspect may include any of hormones, drugs, or cells. In some embodiments, bioactive agents may be held in osmotic pumps and released by osmotic drive. Release mechanisms such as osmotic pumps provide a level of control and predictability to bioactive agent release, but the mechanism remains relatively passive and without means of intervention. Other embodiments of the invention, however, may include more active mechanisms for bioactive agents release or delivery, as could be provided by electrically driven pumps, or by piezoelectric elements that allow or promote the release stored bioactive agents in response to applied current. Such devices may include power storage elements, or may be provided power by external sources by wired or wireless approaches.

In still other embodiments of the invention, the device may include electrodes or conductive elements that provide electrical stimulation to nerves in the intestine, such resulting neural activity contributing to a net effect of signaling satiety to the brain. In some embodiments, satiety-related neuronal activity may further be mediated by endocrine mechanisms. As in embodiments of the invention with powered mechanisms for bioactive agent release, embodiments with electrical capability may include power storage devices, or be enabled to receive energy conveyed from external sources.

In other aspects of the invention, embodiments of the inserted device, with or without an anchor, may provide a platform for bioactive agent delivery, neural stimulus delivery, or radiation therapy delivery, for medical purposes more broad than inducing satiety, or intervening in food transit. For the delivery of some bioactive agents, there may be considerable advantage associated with local delivery of an agent to an intestinal site. Such advantages may include localization of dosing, lack of exposure to stomach acid as occurs in oral delivery, or diminished exposure to the metabolic machinery of the liver and kidney that i.v. drug delivery, or any form of systemic delivery faces. Further, embodiments of the device may accommodate multiple drugs, in some embodiments the release of such multiple drugs may be independently controlled.

Digestive System Context of Invention

The description now addresses the digestive system, the digestive process, and aspects of the endocrinology and neurophysiology of satiety as they relate to embodiments of the invention. The adult duodenum is about 20-25 cm long and is the shortest, widest, and most predictably placed part of the small intestine. The duodenum forms an elongated C-shaped configuration that lies between the level of the first and third lumbar vertebrae in the supine position. Susan Standring (ed.), Gray's Anatomy, $39^{th}$ Ed., 1163-64 (2005), provides a standard reference. Returning to FIG. 1 for reference and further detail of aspects of the digestive system, the first part of the duodenum, often referred to as the duodenal bulb 10a, is about 5 cm long and starts as a continuation of the duodenal end of the pylorus 8. This first part of the duodenum passes superiorly, posteriorly and laterally for 5 cm before curving sharply inferiorly into the superior duodenal flexure 465, which marks the end of the first part of the duodenum. The second part of the duodenum, often called the vertical duodenum 10b, is about 8-10 cm long. It starts at the superior duodenal flexure 465 and runs inferiorly in a gentle curve towards the third lumbar vertebral body. Here, it turns sharply medially into the inferior duodenal flexure 475 which marks its junction with the third part of the duodenum. The third part of the duodenum, often called the horizontal duodenum 10c, starts at the inferior duodenal flexure and is about 10 cm long. It runs from the right side of the lower border of the third lumbar vertebra, angled slightly superiorly, across to the left and ends in continuity with the fourth part of the duodenum in front of the abdominal aorta. The fourth part of the duodenum is about 2.5 cm in length; it starts just to the left of the aorta and runs superiorly and laterally to the level of the upper border of the second lumbar vertebra. It then turns antero-inferiorly at the duodenojejunal flexure and is continuous with the jejunum. Some embodiments of the present invention take advantage of this predictable configuration of the small intestine to provide duodenal/small intestinal implants that do not require anchoring within the pylorus or stomach, as described more fully below.

The digestive process starts when consumed foods are mixed with saliva and enzymes in the mouth. Once food is swallowed, digestion continues in the esophagus and in the stomach, where the food is combined with acids and additional enzymes to liquefy it. The food resides in the stomach for a time and then passes into the duodenum of the small intestine to be intermixed with bile and pancreatic juice. Mixture of the consumed food with bile and pancreatic juice makes the nutrients contained therein available for absorption by the villi and microvilli of the small intestine and by other absorptive organs of the body.

The presence of partially digested food within the stomach and small intestine initiates a cascade of biological signals that create satiety signals and contribute to the cessation of food intake. One such satiety signal is initiated by the release of cholecystokinin (CCK). Cells of the small intestine release CCK in response to the presence of digested foods, and in particular, in response to dietary fat, fatty acids, small peptides, and amino acids. Elevated levels of CCK reduce meal size and duration and may do so through a number of different mechanisms. For example, CCK may act on CCK-A receptors in the liver and within the central nervous system to induce satiety signals. CCK stimulates vagal afferent fibers in both the liver and the pylorus that project to the nucleus tractus solitarius, an area of the brain that communicates with the hypothalamus to centrally regulate food intake and feeding behavior. CCK also stimulates the release of enzymes from the pancreas and gall bladder and inhibits gastric emptying. Because CCK is a potent inhibitor of gastric emptying, some of its effects on limiting food intake may be mediated by the retention of food in the stomach.

Cells of the small intestine (particularly L cells) also release glucagon-like peptide 1 (GLP-1) and oxyntomodulin (OXM) in response to nutrient signals of digestion. Elevated levels of GLP-1 and OXM are associated with satiety signals and the cessation of food intake. These hormones may signal satiety by activating receptors on afferent vagal nerves in the liver and/or the GI tract and/or by inhibiting gastric emptying.

Pancreatic peptide (PP) is released in proportion to the number of calories ingested, and in response to gastric distension. Elevated levels of PP have been shown to reduce food intake and body weight. PP may exert some of its anorectic effects via vagal afferent pathways to the brainstem, as well as through more local effects, such as by suppression of gastric ghrelin production.

Peptide $YY_{3-36}$ ($PYY_{3-36}$) is another biological signal whose peripheral release may be correlated with reduced food intake and/or the cessation of eating. Specifically, low levels of $PYY_{3-36}$ have been correlated with obesity while its administration decreases caloric intake and subjective hunger scores. Intravenous administration of $PYY_{3-36}$ may reduce food intake through its effects of suppressing ghrelin expression, delaying gastric emptying, delaying various secretion from the pancreas and stomach and increasing the absorption of fluids and electrolytes from the ileum after a meal.

Insulin and leptin are two additional biological signals that regulate satiety and eating behavior. Through parasympathetic innervation, beta cells of the endocrine pancreas release insulin in response to circulating nutrients such as glucose and amino acids, and in response to the presence of GLP-1 and gastric inhibitory peptide (GIP). Insulin stimulates leptin production from adipose tissue via increased glucose metabolism. Increased insulin levels in the brain leads to a reduction in food intake. Elevated leptin levels also decrease food intake and induce weight loss. Insulin and leptin have also been implicated in the regulation of energy expenditure since their administration induces greater weight loss than can be explained by reduction in food intake alone. Both insulin and leptin act within the central nervous system to inhibit food intake and to increase energy expenditure, most likely by activating the sympathetic nervous system. Insulin's effects to decrease food intake also involve interactions with several hypothalamic neuropeptides that are also involved in the regulation of feeding behavior such as, by way of example, NPY and melanocortin ligands.

Other hormones or biological signals that are involved in the suppression or inhibition of food intake include, by way of example, GIP (secreted from intestinal endocrine K cells after glucose administration or ingestion of high carbohydrate meals; enterostatin (produced in response to dietary fat; amylin (co-secreted with insulin from pancreatic beta cells); glucagon, gastrin-releasing peptide (GRP), somatostatin, neurotensin, bombesin, calcitonin, calcitonin gene-related peptide, neuromedin U (NMU), and ketones.

In relation to embodiments of the present invention, when the passage of partially digested food or chyme is partially impeded within the duodenum of the small intestine and the flow rate through this area is reduced (or to express the same phenomenon in another way, as residency time is increased), the emptying of the stomach and the duodenum will occur more slowly. This slowing, by itself, may create extended feelings of satiety and thus lead to a decrease in food intake (due to the longer retention time of food in the stomach). The slowing of the passage of food also provides more time for the partially digested food to interact with chemoreceptors, stretch receptors, and mechanoreceptors along the GI tract so that stimulation of satiety signals may be increased and/or prolonged, which may, in turn, lead to a reduction in food intake during an eating period and/or longer periods between food intake.

In addition to keeping partially-digested food within the small intestine for an extended period of time, the methods and devices of the present invention may also enhance and/or prolong the release of satiety signals by releasing signals into the small intestine themselves. For example, in some embodiments, the methods and devices of the present invention may release nutrient products of digestion to stimulate chemoreceptors to cause the release of hormones and/or other molecular signals that contribute to the creation of satiety signals. In another embodiment, the methods and devices of the present invention may exert a small amount of pressure on the walls of the GI tract to stimulate stretch and/or mechanoreceptors to generate and send satiety signals to the brain. In another embodiment, the methods and devices of the present invention may release signals, such as, by way of example, nutrient by-products of digestion of food, to stimulate chemoreceptors as described above and may exert a small amount of pressure on the walls of the small intestine as described above to contribute to the generation of satiety signals.

Device with Flow Reduction Elements, and Embodiments with an Anchoring Member

The methods and devices of the present invention may contribute to weight loss and the treatment of obesity by covering portions of the walls of the small intestine, thus blocking some nutrient uptake and/or interrupting or reducing the intermixing of the digestive fluids. In some embodiments, the methods and devices of the present invention may further include a central tube which funnels a portion of the consumed food through the small intestine without being fully digested or absorbed. In these manners, the methods and devices of the present invention may inhibit the absorption of partially digested food materials. The partially digested food materials are then passed to the large intestine for elimination with limited caloric absorption by the body.

Figure 2:
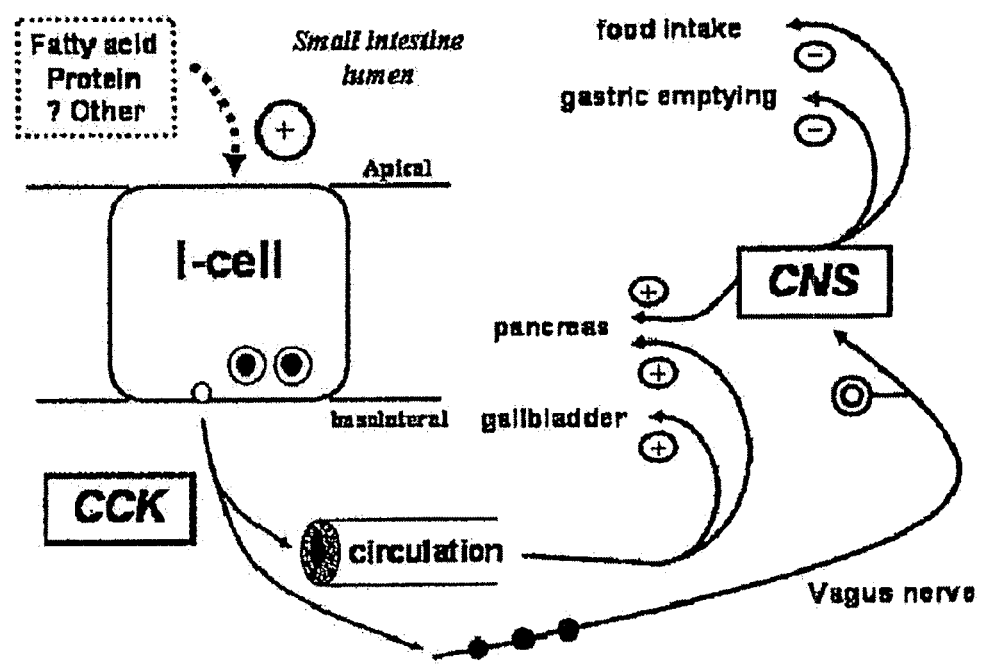
FIG. 2 depicts several exemplary mechanisms through which satiety signals may be generated.

FIG. 2 depicts several exemplary non-limiting mechanisms through which satiety signals may be generated. In this FIG. 2, a by-product of digestion, such as a fatty acid or other protein, stimulates an L-cell of the small intestine to release CCK locally and into the circulation. CCK released locally may stimulate vagal afferent nerve fibers in the area to generate satiety signals to the central nervous system (CNS). CCK that enters the circulation may travel to the liver to stimulate vagal afferent nerve fibers in the liver to generate satiety signals to the CNS. CCK in the circulation may travel to the gall bladder and pancreas to upregulate the digestion-related activities of these organs. CCK in the circulation also may travel to the CNS itself to contribute to the creation of a satiety signal. Once satiety signals are received and integrated within the CNS, the CNS may trigger physiological effects that serve to contribute to a feeling of fullness and/or the cessation, slowing or reduction of food intake.

Figure 3:
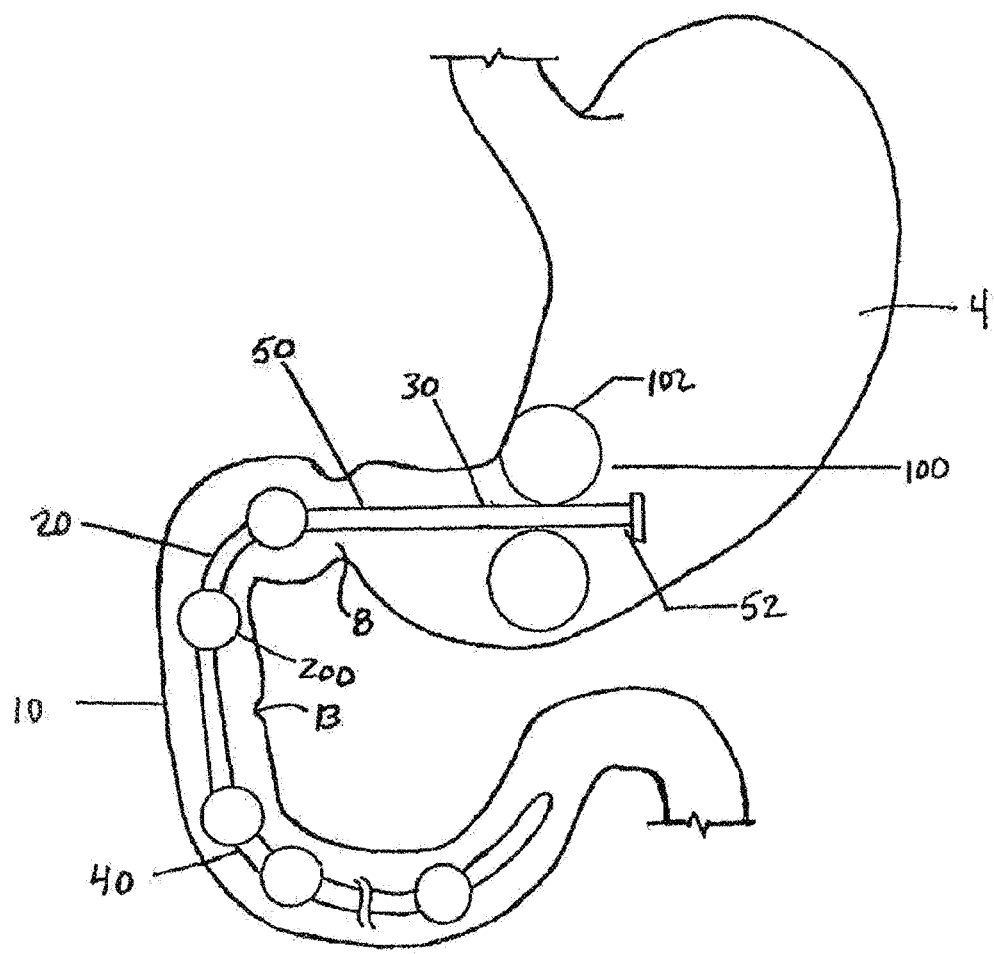
FIG. 3 is a perspective view of one embodiment of a duodenal/small intestinal insert in accordance with the present invention positioned inside the stomach and small intestine.

Turning now to embodiments of the invention, FIG. 3 shows an exemplary small intestinal insert 20 made in accordance with the present invention that may contribute to the creation of satiety signals. The insert 20 is positioned in the stomach 4 and small intestine 10. The insert 20 has a proximal portion 30 and a distal portion 40, and a central tube 50 that extends from the proximal portion 30 to the distal portion 40. One or more flow reduction elements 200 that are sized to fit within the small intestine 10 may be attached to the central tube 50. While not required, the portion of the central tube 50 near the ampulla of Vater 13 generally will not include a flow reduction element 200 so that the introduction of bile and pancreatic fluid into the small intestine is not impeded.

In some embodiments, the central tube 50 has an anchoring member 100 near its proximal end 52, with the anchoring member 100 securing the proximal end 52 of the central tube 50 in the antrum 7 of the stomach. The anchoring member 100 is sized so that it will not pass through the pylorus 8. In this way, embodiments of the present invention including an anchoring member anchor the flow reduction elements 200 within the small intestine. In some embodiments, the anchoring member may be established by one or more inflatable balloons 102 that when inflated are larger than the pylorus 8. The inflatable balloons 102 may be deflated for delivery into the stomach and then inflated inside the stomach. The inflatable balloons 102 may also be deflated for later removal using endoscopic techniques.

As will be described in further detail below, embodiments of flow reduction elements 200 may assume many configurations, and may vary further with regard to physical features such as composition, nature of the surface, and porosity of the bulk material. Some further exemplary embodiments of flow reduction elements 200 are depicted in FIGS. 16-25. In some embodiments, as depicted in FIG. 16, the central tube or member, also referred to as an elongated member, may, itself, be configured into a form that reduces chyme flow in the duodenum. A functional property that embodiments of flow reduction elements have in common is that they slow the transit of digesting food without blocking it, and within clinically appropriate guidelines. The process of slowing the transit rate may also have effects on the composition of the digesting food material, such as varying its biochemical profile with regard to the nutritional compounds being metabolized. Chemical receptors and nerves of the duodenum are sensitive to the biochemical profile of metabolites within the chyme, and participate in the coordination of physiology of digestion and satiety and hunger, accordingly. As such, by altering the flow rate and hence, the biochemical profile of chyme, embodiments of the inventive small intestinal insert contribute to the generation of signals associated with satiety. Flow reduction elements may further effect the composition of the digesting food material by the mixing action the flow reduction elements may provide.

The length of the central tube 50 may be established depending on the therapeutic result desired. For example, the central tube 50 and the one or more attached flow reduction elements 200 may extend into a portion of or through the entire duodenum 10. On some patients the central tube 50 and the one or more attached flow reduction elements 200 may extend past the duodenum 10 and into the jejunum 12. It is anticipated that differing lengths of central tubes and differing numbers and configurations of the flow reduction elements may be used by a physician to treat various body types and metabolic demands. In one example, if a patient is 20% overweight, a physician might select a length of central tube 50 with attached flow reduction elements 200 that permit absorption of only 80% of the nutritional potential of a typical daily intake of calories. This reduction of caloric intake over time could lead to an appropriate amount of weight loss in the patient.

Figure 4:
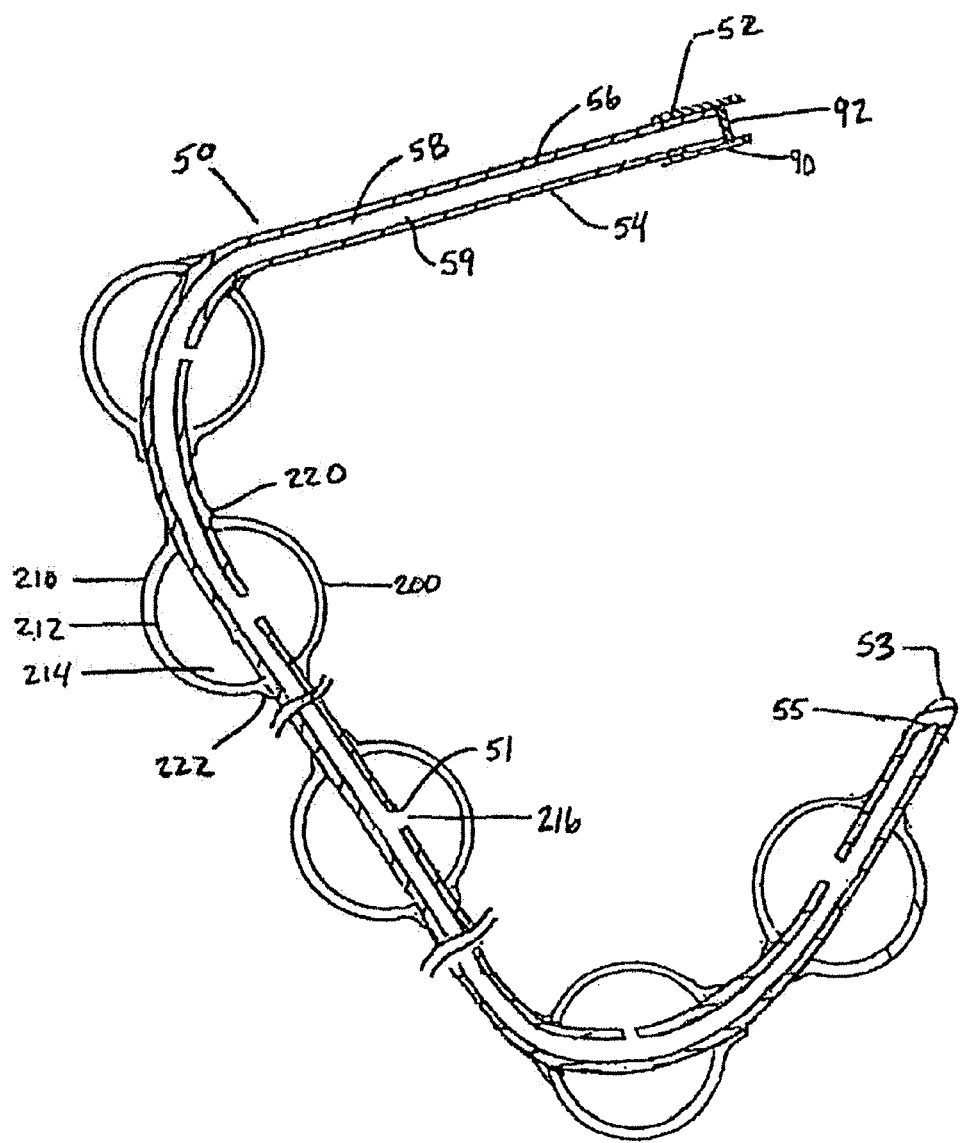
FIG. 4 is a partial section view of a central tube illustrating attached flow reduction elements and a central lumen.

FIG. 4 shows an embodiment of the invention with a central tube 50 that includes an outer wall 54 and an inner wall 56 that define an interior space 58. The interior space 58 forms an inner lumen 59 that may be continuous from the proximal end 52 of the central tube 50 to just short of the distal end 53 of the central tube 50. The distal end 53 of the central tube 50 is sealed at a point 55 so that fluid introduced into the central tube 50 does not leak out distally into the small intestine. In some embodiments a valve 90 may be located substantially at the proximal end of the inner lumen 59. The valve 90 may be a self sealing valve that has a septum 92 that may be accessed by a needle or blunt tip tube for introduction of fluid into the inner lumen 59. The valve 90 also may be accessed so that the fluid inside the inner lumen 59 of the central tube 50 may be aspirated for removal. It is to be understood that the valve type is not limited to a septum type valve only, and that other types of mechanical valves may also be used in place of the septum valve described. Particular embodiments of the present invention are adapted to accept fluids in this manner so that the devices of the present invention may be implanted in a deflated configuration and later expanded into an inflated configuration.

As shown in FIG. 4 and as mentioned above, one or more flow reduction elements 200 may be attached to the central tube 50. In some embodiments the diameter of each flow reduction element 200 may be concentric with the axis of the central tube 50. In the embodiment depicted in FIG. 4, each flow reduction element 200 has an outer wall 210, an inner wall 212, and an inner space 214. At or near its proximally-oriented surface 220 and also at or near its distally-oriented surface 222, each flow reduction element 200 may be attached to the central tube 50 with the inner space 214 of the flow reduction element 200 in fluid communication with the lumen 59 of the central tube 50, such that the inner space 214 surrounds the outer wall 54 of the central tube 50. Each flow reduction element 200 may be attached to the central tube 50 by, for example, adhesives, heat bonding, mechanical restraint or other suitable methods.

As also depicted in FIG. 4, the central tube 50 may be formed with plural inlet/exit ports 216 that are located inside respective flow reduction elements 200. More specifically, each port 216 is formed completely through the central tube wall 51 to establish a pathway for fluid communication between the inner lumen 59 of the central tube 50 and the inner space 214 of the respective flow reduction elements 200. Consequently, the inner lumen 59 of the central tube 50 may be used to introduce fluid into the inner spaces 214 of the flow reduction elements 200 and to inflate the flow reduction elements 200 from a collapsed configuration, in which insertion and removal of the flow reduction elements 200 is facilitated, to an inflated configuration shown in FIG. 4, in which resistance to food passage is increased to induce satiety. Thus, as suggested earlier, the flow reduction element or elements 200 in this embodiment act as balloons that may be deflated and collapsed around the central tube 50 for introduction into the small intestine and then inflated to the desired diameter once in position.

Embodiments of the flow reduction elements 200 may assume other forms, such as coils, ribs, fans, baffles, either peripherally-mounted or centrally-mounted, as well as sleeves, mesh cages or baskets. Embodiments such as these are described further, below, in the section entitled "Further embodiments of the invention", which also includes description of embodiments with biodegradable components, active biomaterial release mechanisms, and nerve stimulation features, and as depicted in FIGS. 15-31.

In some embodiments, individual flow reduction elements 200 of the present invention may be elastic balloons or inelastic balloons. When an elastic balloon material is used to establish a flow reduction element 200, the flow reduction element 200 inflates to a diameter that is dependent on the volume of fluid introduced into the inner space of the flow reduction element. This embodiment permits adjustment of the balloon size as determined by the physician. If the balloon is too small, for instance, additional fluid could be introduced to enlarge the balloon diameter. Alternatively, if the balloon is too large, additional fluid could be removed to shrink the balloon diameter. It is understood that an alternate embodiment consisting of an inelastic balloon that inflates to a diameter that is independent of a volume of fluid introduced into its inner space is also included within the present invention. The diameter of this type of balloon is fixed when manufactured and does not permit in situ adjustment of the balloon size. However, this type of balloon prevents possible over inflation and rupture if too much fluid is introduced into the balloon.

The flow reduction elements 200 shown in FIG. 4 have the shape of a round sphere. However, other shapes are contemplated and any shape that effectively functions to inhibit the passage of partially digested food in the small intestine is acceptable in accordance with the present invention. It is understood that the ability of the small intestinal insert to remain within the small intestine may be affected by the shape, orientation and tautness of the flow reduction elements 200. For example alternate shapes such as ovoid, elliptical, elongated ellipse and even irregular non-geometrical shapes could be used in accordance with the present invention.

Figure 5:
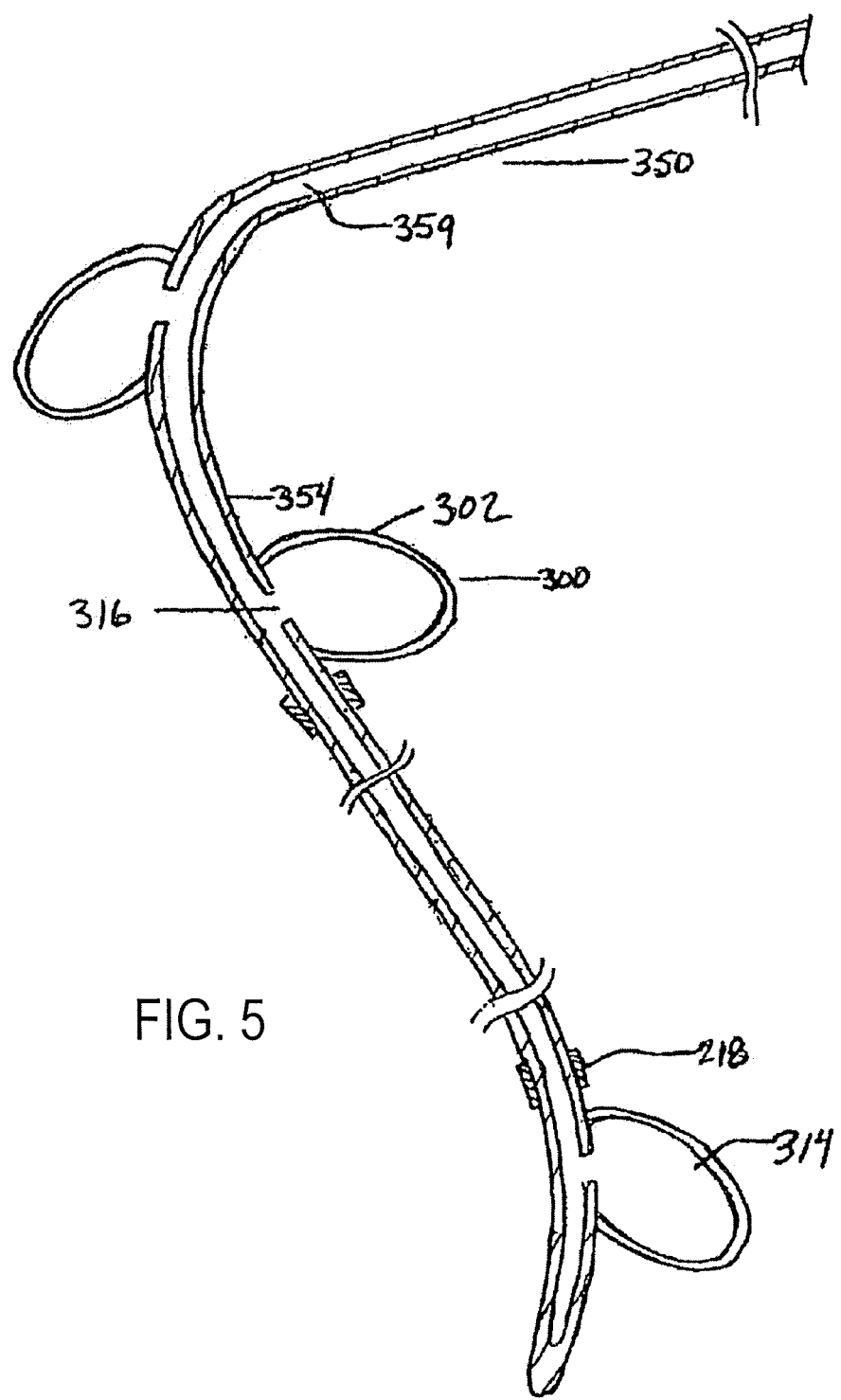
FIG. 5 is a partial section view of a central tube illustrating eccentrically attached flow reduction elements and a central lumen.

FIG. 5 illustrates an alternative embodiment of the present invention in which one or more flow reduction elements 300 are eccentrically attached to a central tube 350. In this embodiment the axis or diameter of the flow reduction element or elements 300 is not concentric with the axis of the central tube. The outer wall 302 of the flow reduction element is attached to the side of an outer wall 354 of the central tube 350. An inner space 314 of each flow reduction element 300 is eccentric relative to the axis of the central tube 350 and is in fluid communication with an inner lumen 359 of the central tube 350 through a respective opening 316. As was the case with the embodiment shown in FIG. 4, in the embodiment shown in FIG. 5 the inner lumen 359 may be used to introduce and remove fluid into the inner space 314 of the flow reduction element 300 to move the flow reduction element 300 between inflated and deflated configurations.

In some embodiments of the present invention, the flow reduction elements 300 may be inflated with a fluid, including a liquid and/or a gas. In some embodiments, the gas may be, for example, air, nitrogen or carbon dioxide. In another embodiment a liquid may be, for example, water or water mixed with other solutions. Any appropriate inflation medium may be modified to deliver bioactive materials or other signals that may diffuse from the insert of the present invention into the small intestine to trigger biological signals of satiety. When bioactive materials are delivered through an inflation medium, the central tube and/or flow reduction elements should be permeable to the bioactive materials. Porosity may be adjusted to control the diffusion rate of the bioactive materials.

When inflating the flow reduction elements of the present invention, it may be important for the physician to monitor the flow reduction element 300 location in the small intestine and the diameter of the flow reduction element relative to the diameter of the small intestine. For this purpose, the flow reduction element may be inflated with a radiopaque fluid that is visible on X-ray. When the flow reduction element contains radiopaque fluid, a physician may non-invasively visualize the size and placement of the flow reduction element(s) from outside the patient's body. This knowledge enables the physician to adjust the size and/or placement of the flow reduction element(s). Likewise radiopaque marker bands 218 as shown in FIG. 5 may be placed around the central tube to facilitate visualization of the central tube's location in the small intestine. The radiopaque marker bands 218 may be placed at predetermined intervals so that the distance inside the small intestine may be used as depth markers and may be measured from outside of the body.

The central tube and flow reduction elements of the present invention may be flexible. In some embodiments, they may be constructed of a polymeric material that may be easily formed or extruded and delivered with the aid of an endoscope by known techniques. A central tube 50 that is soft and flexible will contour to the anatomy of the gastro-intestinal tract and provide less irritation of the stomach and intestinal lining.

Figure 6:
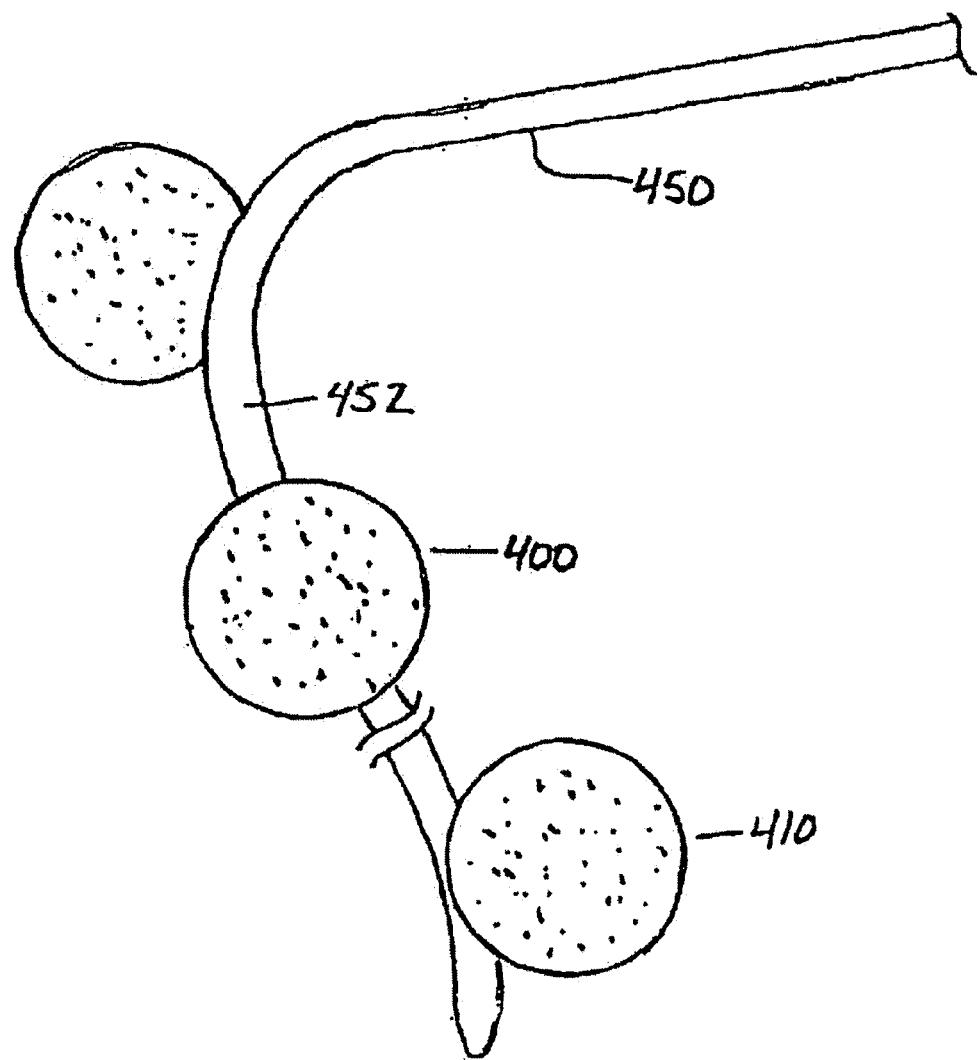
FIG. 6 is a perspective view of an alternative embodiment showing an elongated member and illustrating attached flow reduction elements.

FIG. 6 shows an alternative embodiment of the invention with flow reduction elements that are generally self-expanding, and do not necessarily include a central lumen. These embodiments include a central shaft 450 around which flow reduction elements are concentrically attached 400 and/or are eccentrically attached 410. The elements 400 and 410 may be attached to the central shaft 450 by, for example, heat fusing, adhesives or other suitable methods as known in the art. These flow reduction elements 400 may be made from material that may be folded or collapsed to a first volume suitable for insertion with the aid of an endoscope and then may self expand to a second volume suitable for restricting the flow of partially digested food according to the present invention. These flow reduction elements may be made from materials, or materials may be configured so as to take the form of such as, by way of example, a sponge, a foam, a hydrogel, or springs that may be compacted into a small volume and then self expand to a predetermined shape and volume when unrestricted. Gel- or sponge-based embodiments may include open cell or closed cell forms. In addition to having features that allow such gel- or sponge-based embodiments to be collapsible and expandable for deployment, such embodiments typically have a high surface area which is beneficial in embodiments that may include bioactive agents, and may further be conducive to purposes of biodegradability. Another foam-related embodiment is described below in the section entitled "Further embodiments of the invention", and depicted in FIG. 23. Because the flow reduction elements self expand, the need for an inflation system is eliminated and this embodiment represents a simple mechanical design. These flow reduction elements may also be impregnated with bioactive materials or other signals that may trigger biological signals of satiety.

The central shaft 450 of an embodiment such as that depicted in FIG. 6 may be solid and without an inner lumen or inner space. In another embodiment the central shaft 450 may include a passageway for consumed food so that the food may pass through the small intestine without being fully absorbed.

Figure 7:
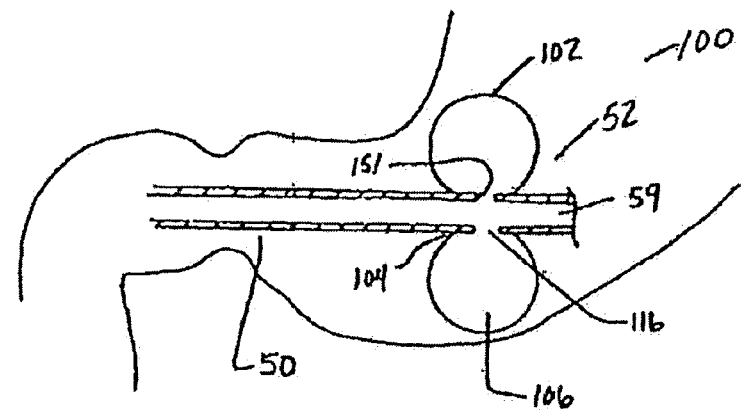
FIG. 7 is a perspective section view of a central tube and an anchoring member.

Turning now to various anchoring members that may be used in accordance with the present invention, FIG. 7 depicts one such member. In FIG. 7, the central tube 50 has an anchoring member 100 near its proximal end 52. As stated earlier, the anchoring member 100 may be established by one or more inflatable balloons 102. These balloons 102 may be eccentrically attached to the central tube at point 104 near the proximal end 52 of the central tube 50. These balloons may be formed in many shapes and are not limited to the spherical shape shown. The central tube may be formed with an opening 116 for each respective balloon 102 so that a pathway for fluid communication is established between the inner lumen 59 of the central tube 50 and the inner space of each balloon 106. The inner lumen 59 is used to introduce fluid into the inner space of the balloon 106 and inflate the balloon 102 from a first volume in a collapsed state to a second volume or inflated state.

When the one or more balloons 102 of the anchoring member 100 are fully inflated, they secure the proximal end of the central tube 52 within the antrum of the stomach. The one or more inflatable balloons 102 have a combined cross sectional diameter greater than the diameter of the pyloric valve to prevent migration across the pylorus. The inflatable balloons 102 may be inflated and deflated by adding or removing fluid from the central tube inner lumen 59. The inflatable balloons 102 may be connected to the same central tube inner lumen 59 as the one or more flow reduction elements attached to the central tube and may be inflated simultaneously with the flow reduction elements. The central tube 50 may also have more than one inner lumen so that the inflatable balloons 102 and individual one or more flow reduction elements may be inflated and deflated independently as well.

Figure 8:
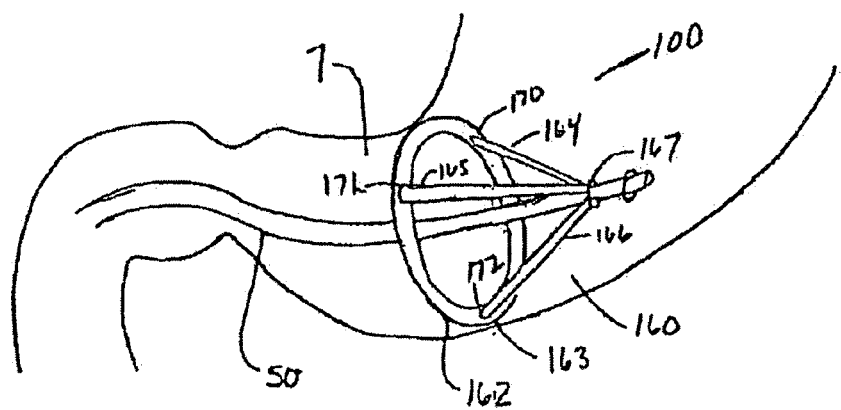
FIG. 8 is a perspective view of an alternative embodiment of a central tube and an anchoring member.

FIG. 8 illustrates another embodiment of the invention, wherein an anchoring member 100 of the present invention is deployed in the antrum 7. In this embodiment, a central tube 50 is attached to an inverted umbrella skeleton 160. This skeleton 160 has a ring 162 that surrounds the central tube 50 and is supported by struts. In the depicted embodiment the ring 162 is supported by three struts 164, 165, and 166, however more or fewer struts may be successfully employed. In the embodiment depicted in FIG. 8, the struts are joined together at the central tube 50 at point 167 and attached to the ring 162 at points 170, 171 and 172. The ring 162 of this anchor configuration may be made from, by way of example, flexible plastic material or flexible wire and has a diameter significantly larger than the diameter of the pyloric valve. This umbrella skeleton 160 may be collapsed around the central tube 50 for insertion into the stomach with the aid of an endoscope. As the device is released from the endoscope, the umbrella skeleton 160 may spring out and assume a configuration similar to that shown in FIG. 8. The struts 164, 165 and 166 may be made from, by way of example, plastic, metal or from plastic covered metal. The edge of the ring which is in contact with the antrum walls 163, may be constructed to assist in securing the umbrella ring 162 to the walls of the antrum. In some embodiments, the surface may be roughened to increase surface friction or the wall may have protrusions or barbs that physically attach to the stomach lining.

Device Without an Anchoring Member

Figure 9:
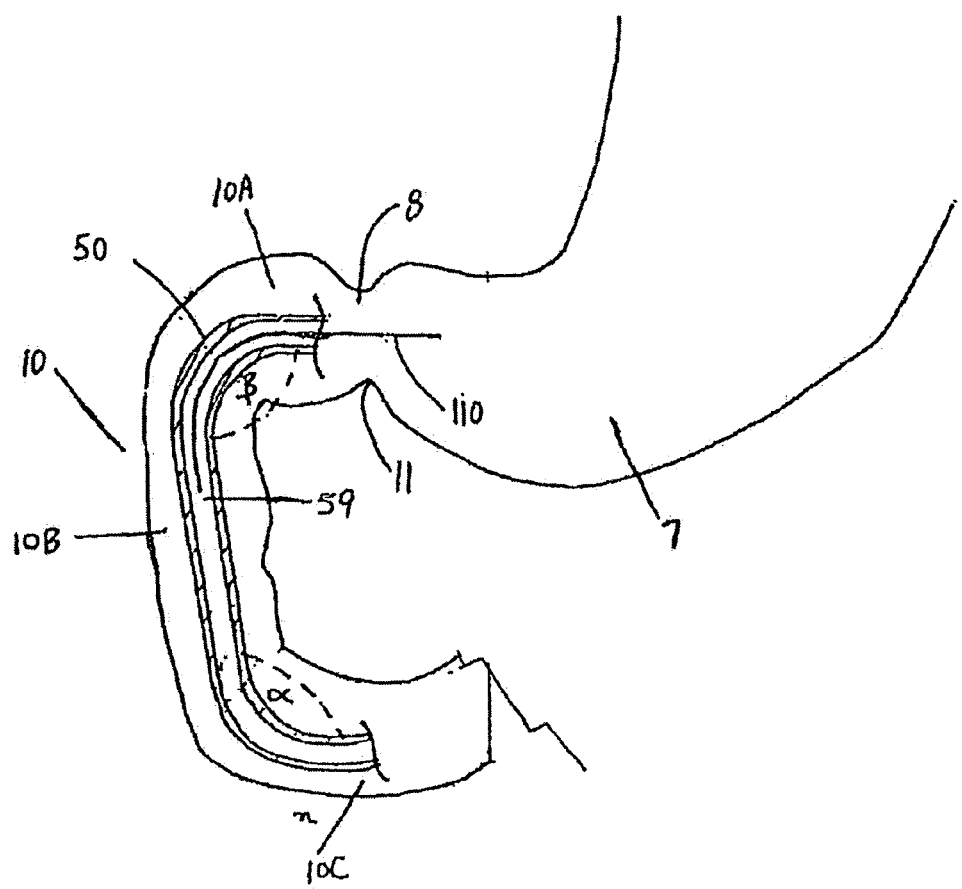
FIG. 9 is a section view of a central tube of the present invention that may lodge in the small intestine for a period of time without any anchoring to the stomach or pylorus.

FIG. 9 shows a central tube or elongated member 50 of the present invention that may lodge and remain in the small intestine for a period of time without any anchoring to the stomach or pylorus. Embodiments of the present invention that can lodge and remain within the small intestine for a period of time without any anchoring to the stomach or pylorus do so by (i) adopting a central tube with appropriately placed angles that mimic the contours of the small intestine; and (ii) flow reduction elements of an appropriate diameter that help to hold the intestinal insert in place. In one embodiment, while not required, these flow reduction elements can have an abrasive surface or anchoring barbs that can help them adhere to the walls of the small intestine.

In FIG. 9, the first three parts of the duodenum, including the duodenal bulb 10A, the vertical duodenum 10B, and the horizontal duodenum 10C are depicted. The flow reduction elements of the depicted embodiment have been removed for clarity. Distal to the pylorus 8 and immediately after entering the duodenum 10, the central tube 50 may assume a sharp bend of radius β between the duodenal bulb 10A and the vertical duodenum 10B, and a sharp bend of radius α between the vertical duodenum 10B and horizontal duodenum 10C. In some embodiments the radius β and the radius α may be between about 45 degrees and about 110 degrees. In another embodiment the radius β and the radius α may be between about 60 degrees and about 100 degrees such that the central tube 50 bends to follow or correspond to the inner lumen of the duodenum 10 at these locations that contain predictably configured bends. In another embodiment the radius β and the radius α may be about 80 degrees. While most embodiments of the present invention will include lengths that require adoption of angle β and angle α, shorter devices adopting one or the other are also included within the scope of the present invention. In these described embodiments of the present invention, it may be advantageous that the central tube 50 be flexible enough to conform to the sharp angulations of the small intestine to avoid kinking. One or more flow reduction elements with a diameter about equal to that of the small intestine are also included along the length of the central tube 50. In some embodiments, this diameter is about 3 cm; in other embodiments this diameter is about 4 cm.

To stabilize an intestinal insert in situ without the need for an anchoring element, the central tube or elongated member 50 may be pre-formed with a configuration that conforms to the duodenal angulations prior to insertion in the body. This embodiment of the present invention may be constrained in a straight configuration by a stiffening rod 110 placed down the inner lumen 59 of the central tube 50 as shown. This stiffening rod 110 may be placed into a separate lumen designed to house this stiffening rod or may be imbedded in the wall of the central tube 50. Upon insertion into the patient with the aid of an endoscope, when the central tube 50 reaches the location of the sharp bends in the duodenum 10, the stiffening rod 110 may be withdrawn, thereby allowing the central tube 50 to assume a pre-formed shape.

In another embodiment that stabilizes in situ without an anchoring member, the central tube or elongated member 50 may have a shape memory alloy wire embedded inside the central tube wall 51 or residing in the inner lumen 59. This shape memory alloy wire has a pre-set bend configuration with a radius β and a radius α that matches or corresponds to the bend configuration of the duodenum and is positioned in the central tube 50 at the corresponding location. Upon insertion into the patient with the aid of an endoscope, when the central tube 50 reaches the location of the sharp bend in the duodenum 10 and the shape memory alloy wire reaches a pre-set transition temperature equal to body temperature or about 37° C., the wire assumes the programmed shape and forces the central tube 50 and the central tube wall 51 to assume the same shape.

In another embodiment, the central tube or elongate member 50 may have a spring embedded inside the central tube wall 51 or inner lumen 59. This spring could be pre-shaped to the anatomy of the wall of the small intestine. The spring is held straight during delivery and conforms to the small intestine anatomy after release, and such shape enables the device to remain in place. The shape enables the device to remain in place. In one embodiment, due to its configuration that matches or corresponds to the predictable placement and configuration of the small intestine, the device can remain in place for a period of time within the small intestine without anchoring to the stomach or pylorus of the stomach.

While the present embodiments of the present invention can remain in the small intestine for a period of time without anchoring to the stomach or pylorus, they are not intended to remain indefinitely. In some embodiments, the inserts are endoscopically removed after a predetermined period of time. In other embodiments, the inserts may be formed of one or more biodegradable materials that are eventually degraded and eliminated from the body. The rate of biodegradability of any embodiment of the inventive device may be adjusted by varying the biodegradable aspects of the embodiment, thus allowing for a manufacturing route to control the residency time in the intestinal tract to a clinically appropriate level. Biodegradable composition may be varied in qualitative terms, by varying the composition of the materials. Biodegradability of devices may also be varied in quantitative terms, for example, by varying the quantity of material at a location vulnerable to biodegradation. For example, varying the thickness of a junction designed for biodegradable vulnerability may be varied in thickness.

Biodegradable aspects of embodiments of the invention are described further below; all embodiments described herein, and all embodiments as depicted in FIGS. 3-12, and 16-31 may have portions that include biodegradable materials, both within the central tube or member, also referred to synonymously as elongate member 50 and/or any of the various embodiments of the chyme flow reduction elements 200. In the description that ensues, some embodiments are used as specifically illustrative examples that are formed wholly or in part from biodegradable materials, but, as stated, all embodiments may include biodegradable materials, even when not specifically identified as such, including embodiments with and without an anchoring member.

Deployment of Inserts and Flow Reduction Elements

Figure 10:
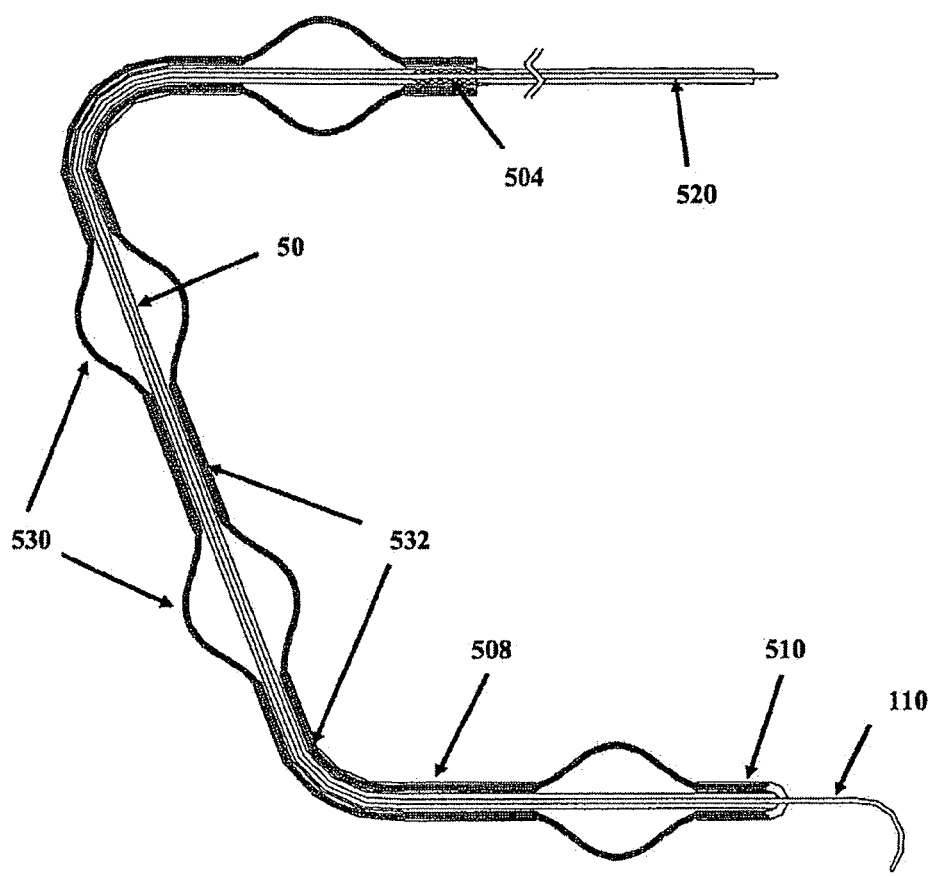
FIG. 10 illustrates a central tube attached to an expandable sleeve, the expandable sleeve allowing expansion of particular segments of the central tube to form flow reduction elements.

The description now turns to considerations related to deployment of the inventive insert, some embodiments of which include flow reduction elements. Flow reduction elements are referenced in a generic sense with the label 200, but some exemplary embodiments make use of different label numbers, for their particular features. FIG. 10 illustrates an embodiment of the present invention where flow reduction elements may be created through the expansion of portions of an expandable sleeve; this embodiment will be used in the context of describing an example of how to deploy a device with flow reduction elements. In the embodiment depicted in FIG. 10, a central tube 50 is attached to an expandable sleeve 508 at the expandable sleeve's distal end 510 near the distal portion of a duodenal/small intestinal insert of the present invention. In a delivery configuration of the depicted embodiment, the opposite proximal end of the central tube 50 is attached to a detachable extension tube 520 that may lock onto a proximal portion of the central tube 50 when the flow reduction elements 530 are expanded (post delivery). One non-limiting method of detachable attachment is the use of one or more screws 504, whereby the extension tube 520 screws into the central tube 50. The central tube 50 may be pre-formed to have a configuration that conforms to the anatomy of the duodenum 10 shown in FIG. 1. A central tube 50 so described would force the expandable sleeve 508 to assume the configuration of the central tube 50. The central tube 50 may be constructed, merely by way of example, of wire, spring, super elastic or shape memory alloys, hollow steel tubing or plastic polymers. In some embodiments a stiffening rod or guide wire 110 may also be inserted through the lumen of central tube 50.

The expandable sleeve 508 herein described is designed to expand at predefined segments to allow the formation of flow reduction elements 530. In some embodiments, the non-expanded segments 532 of expandable sleeve 508 may be coated with a polymer to prevent their expansion. In another embodiment, the flow reduction elements 530 may be covered with a flexible polymer to prevent partially digested food from entering the flow reduction elements 530. In another embodiment, a stiffening rod or guide wire 110 may be inserted through the lumen of central tube 50 to straighten the central tube 50 when the device is delivered into the duodenum.

The expandable sleeve 508 may, merely by way of example be configured as any one or more of a knit, a weave, a mesh or a braid that may be formed, merely by way of example from any one or more of a metal, a wire, a ribbon, a plastic polymer or a biodegradable material.

Figure 11:
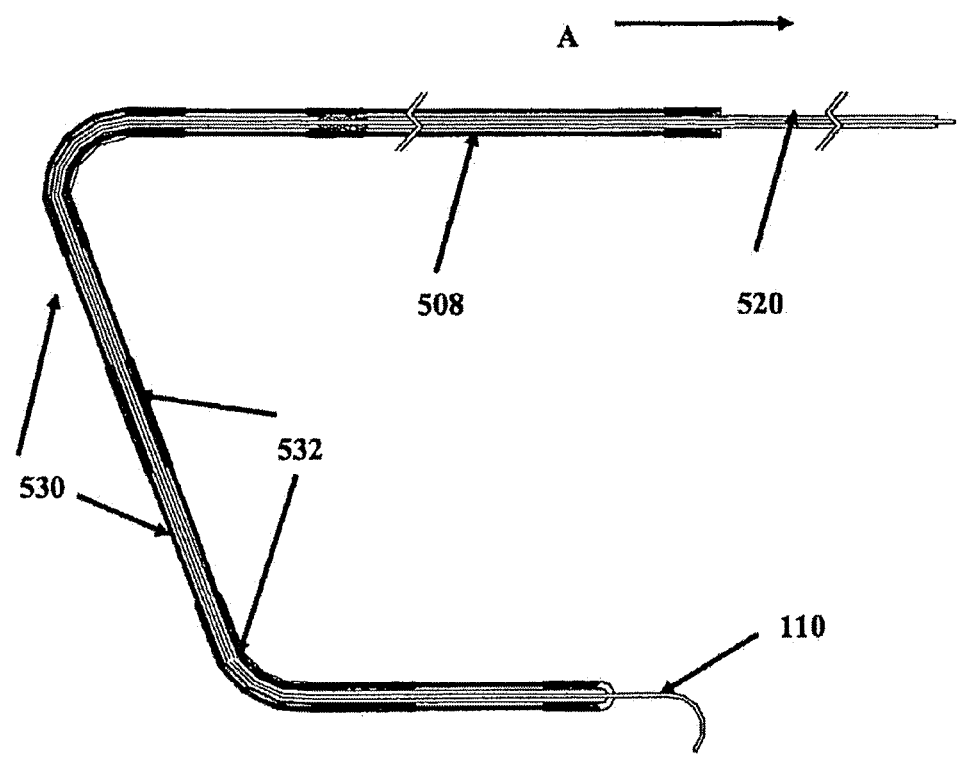
FIG. 11 illustrates an expandable sleeve in a collapsed configuration for insertion into the small intestine.

FIG. 11 illustrates the expandable sleeve 508 consisting of flow reduction elements 530 in a collapsed configuration for insertion into the small intestine. In this configuration a force A is applied to the expandable sleeve 508 to collapse the flow reduction elements 530. The collapsed form may be restrained by a constraining mechanism such as, merely by way of example, a sheath or a tightly wound string, or by applying sustained traction on the proximal end of the expandable sleeve 508. FIG. 11 also shows portions of the central tube that will remain unexpanded 532, a detachable extension tube 520 and a guidewire 110.

The expansion of the flow reduction elements 530 in the embodiments depicted in FIGS. 10 and 11 may occur passively or actively. One example of passive expansion may be the removal of a constraining mechanism to allow the flow reduction elements 530 to expand to an original expanded state. Another non-limiting mechanism can be to release traction on the proximal end of an expandable sleeve 508 to allow the flow reduction elements 530 to expand to an original expanded state.

The flow reduction elements 530 of the embodiments depicted in FIGS. 10 and 11 can expand in a distal to proximal fashion, a proximal to distal fashion or in a central fashion depending on their relative position in relation to, in some embodiments, motion of the expandable sleeve 508 and the central tube 50 to one another. For example, if the proximal end of the flow reduction element lumen is held in the duodenal bulb and the central tube 50 is pulled back, the distal end of the flow reduction element lumen may expand first. Expansion in this direction may be advantageous because the position of the proximal end of the flow reduction element lumen remains in the duodenal bulb.

Figure 12:
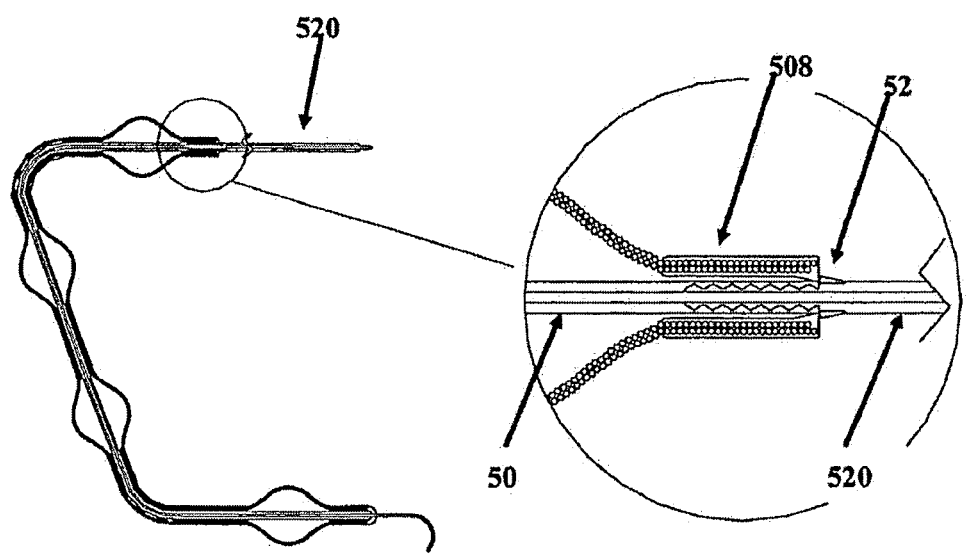
FIG. 12 illustrates one mechanism for keeping flow reduction elements formed with an expandable sleeve in a desired expanded configuration.

FIG. 12 illustrates some embodiments of the present invention that may lock the proximal end of the expandable sleeve 508 to the central tube 50 at a position to keep the flow reduction elements in a desired expanded configuration. Traction on the extension tube 520 retracts central tube 50 until wedge 52 engages the proximal end of the expandable sleeve 508. The central tube 50 may have multiple ratchet-like wedges that may lock the expandable sleeve 508 at different degrees of expansion. The extension tube may be unscrewed from the central tube 50 after deployment of the device and expansion of the expandable sleeve 508.

Biodegradable Features

While the present embodiments of the present invention may remain in the small intestine for a period of time, they are not intended to remain indefinitely. In some embodiments, the inserts are endoscopically removed after a predetermined period of time. In other embodiments, the inserts may be formed or partially-formed of one or more biodegradable materials that are eventually degraded and eliminated from the body. In some embodiments, the device may include some material that is biodegradable and some material that is not biodegradable. In some embodiments that include non-biodegradable materials, the degradation of the biodegradable portions of the device may facilitate the breakdown and eventual elimination of the non biodegradable portions.

Biodegradable is used in a broad sense, so as to include the any type of material breakdown or disintegration of any type that may occur in a biological environment, such environment being defined primarily by the biological host, but also by any microorganisms within the host. Other terms that biodegradability broadly embraces include bioabsorbability and bioerodibility. Biodegradation, per embodiments of the invention, may occur, for example, by dissolution, by effects of pH, such as action of acids, by hydrolytic mechanisms, by hydration, by digestive or enzyme-catalyzed effects such as cleavage, or by physical effects of bodily or muscular movement. An example of biodegradation is provided by the hydrolysis, dissolution, or reaction to pH, or enzymatic lysis that results in a scission of the polymer backbone of an inserted device. Microorganisms such as those that reside in the intestine, may eat or digest polymers, and also initiate a mechanical, chemical, or enzymatic aging. The biodegradable materials of embodiments of the invention are also biologically compatible, as well as are breakdown products of biodegradable materials, as included in embodiments of the present invention. Biodegradable materials may include organic and inorganic compounds. Some representative inorganic compounds are described below in the section related to "device features to accommodate bioactive agents"; in this section, a description of biodegradable polymers is provided for inclusion as embodiments of the present invention.

Figure 30A:
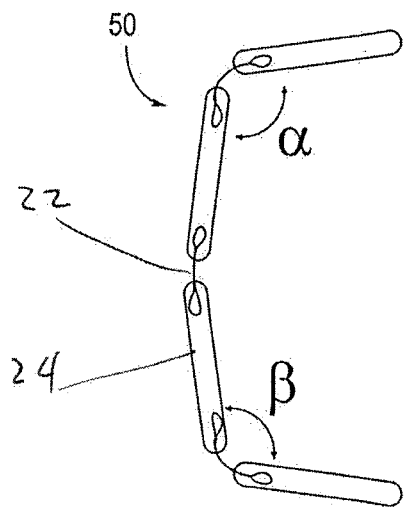
FIGS. 30A-30B depict an embodiment of the central member of an insert that includes biodegradable elements and shape memory elements.
Figure 30B:
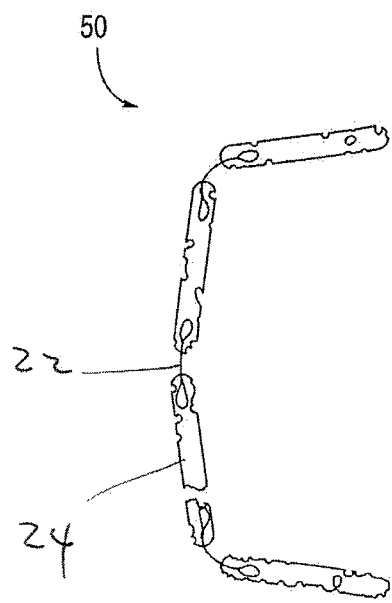
Figure 31A:
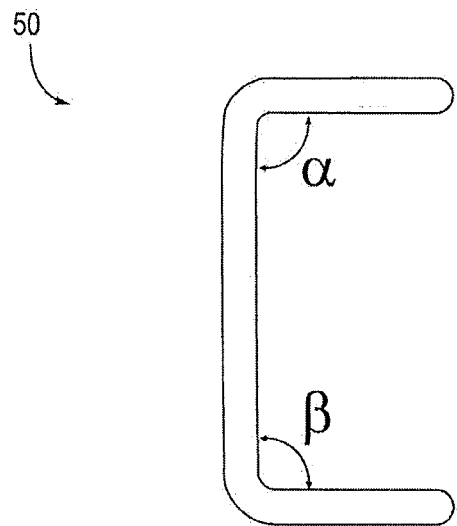
FIGS. 31A-31B depict an embodiment of the central member of an insert that includes a biodegradable shape memory polymeric material.
Figure 31B:
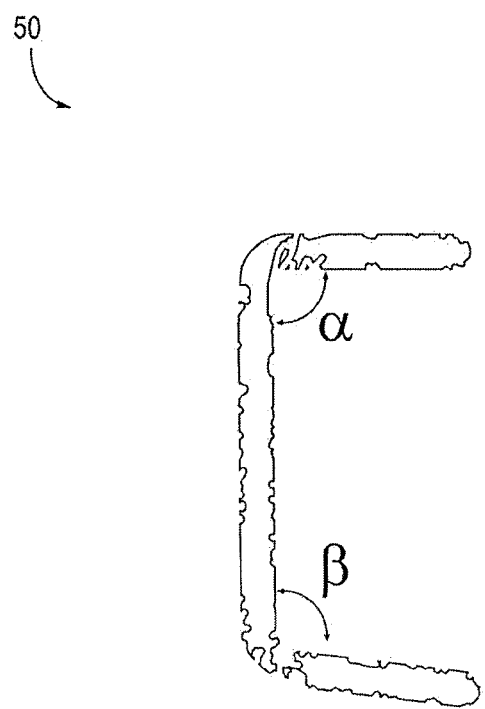

As mentioned above, some embodiments of the invention may include a resilient shape holding portion, and in some embodiments, a shape memory portion that supports the maintenance of an advantageous configuration of the device, particularly with regard to maintenance of angles alpha and beta of the inventive C-shaped duodenal insert device. Metals as well as some polymers are capable of resiliently holding a shape. Shape memory materials include metal alloys as well as biodegradable polymers. Shape memory alloy elements of the device are not biodegradable, but these alloy structural elements may be combined or joined with polymeric elements that are biodegradable, and upon such degradation, the alloy elements are released in a form that allows their elimination. Such embodiments are depicted in FIGS. 30A and 30B, as described below. Other embodiments or the invention may include biodegradable shape memory polymeric elements. Biodegradable shape memory polymers have been described in various publications, including U.S. Pat. Nos. 6,160,084, 6,281,262, 6,388,043, 6,720,402, and US Published Applications US 20050075405A1, US 20030055198A1, US 20040015187A1, US 20040110285A1, US 20050245719A1, and US 20060142794A1. Embodiments of the invention may include any one or more of such shape memory materials, and further, such materials may be joined together in various ways as depicted in FIGS. 31A and 31B.

A variety of natural, synthetic, and biosynthetic polymers are biologically degradable and may be included as materials that comprise embodiments of the intestinal insert device. A polymer based on the C—C backbone tends to be nonbiodegradable, whereas heteroatom-containing polymer backbones confer biodegradability. Biodegradability may be engineered into polymers by the judicious addition of chemical linkages such as anhydride, ester, or amide bonds, among others. The mechanism for degradation is by hydrolysis or enzymatic cleavage resulting in a scission of the polymer backbone. Microorganisms, such as those that reside in the intestine, may eat or digest polymers, and also initiate a mechanical, chemical, or enzymatic aging.

Biodegradable polymers with hydrolyzable chemical bonds are appropriate as materials for a biodegradable intestinal insert. In addition to being biocompatible, the material should meet other criteria, for example, being processable, sterilizable, and capable of controlled stability or degradation in response to biological conditions. The degradation products often define the biocompatibility of a polymer, not necessarily the polymer itself. Poly(esters) based on polylactide (PLA), polyglycolide (PGA), poly-caprolactone (PCL), and their copolymers have been extensively employed as biomaterials. Degradation of these materials yields the corresponding hydroxy acids, making them safe for in vivo use.

Other biodegradable polymers include poly(hydroxyalkanoate)s of the PHB-PHV class, additional poly(ester)s, and natural polymers, particularly, modified poly(saccharide)s, e.g., starch, cellulose, and chitosan. Chitosan is derived from chitin, and is the second most abundant natural polymer in the world after cellulose. Upon deacetylation, it yields the novel biomaterial Chitosan, which upon further hydrolysis yields an extremely low molecular weight oligosaccharide. Chitosan is biocompatible, antibacterial and environmentally friendly polyelectrolyte, thus appropriate for medical devices and as material for controlled release in drug delivery.

Poly(ethylene oxide), PEO, a polymer with the repeat structural unit —$CH_2CH_2O$—, has applications in drug delivery. The material known as poly(ethylene glycol), PEG, is in fact PEO but has in addition hydroxyl groups at each end of the molecule. In contrast to high molecular weight PEO, in which the degree of polymerization, n, might range from $10^3$ to $10^5$, the range used most frequently for biomaterials is generally from 12 to 200, that is PEG 600 to PEG 9000, though grades up to 20,000 are commercially available. Key properties that make poly(ethylene oxide) attractive as a biomaterial are biocompatibility, hydrophilicity, and versatility. The simple, water-soluble, linear polymer may be modified by chemical interaction to form water-insoluble but water-swellable hydrogels retaining the desirable properties associated with the ethylene oxide part of the structure.

Multiblock copolymers of poly(ethylene oxide) (PEO) and poly(butylene terephthalate) (PBT) may also be appropriate for intestinally inserted devices. These materials are subject to both hydrolysis (via ester bonds) and oxidation (via ether bonds). Degradation rate is influenced by PEO molecular weight and content. Additionally, the copolymer with the highest water uptake degrades most rapidly.

A widely used nondegradable polymer is ethylene-vinyl acetate copolymer. This copolymer has excellent biocompatibility, physical stability, biological inertness, and processability. In drug delivery application these copolymers usually contain 30-50 weight percent vinyl acetate. Ethylene-vinyl acetate copolymer membrane acts as the rate-limiting barrier for the diffusion of the drug. In the Type II class of degradable polymers, the conversion of the hydrophobic substituents to hydrophilic side groups is a first step in the degradation process. The tyrosine-derived polycarbonate poly(DTE-co-DT carbonate), may, for example, be an appropriate material for a biodegradable intestinal insert. The material may be made with the pendant group via the tyrosine as either an ethyl ester (DTE) or free carboxylate (DT). Through alteration of the ratio of DTE to DT, the material's hydrophobic/hydrophilic balance and rate of in vivo degradation may be manipulated.

Water-swellable polymer networks may function as hydrogels at one end or as superabsorbers at the other extreme. Hydrogels are characterized by the pronounced affinity of their chemical structures for aqueous solutions in which they swell rather than dissolve. Such polymeric networks may range from being mildly absorbing, typically retaining 30 wt. % of water within their structure, to super-absorbing, where they retain many times their weight of aqueous fluids. Several synthetic strategies have been proposed to prepare absorbent polymers including: polyelectrolyte(s) subjected to covalent cross-linking, associative polymers consisting of hydrophilic and hydrophobic components ("effective" cross-links through hydrogen bonding), and physically interpenetrating polymer networks yielding absorbent polymers of high mechanical strength. These approaches are not mutually exclusive, and materials may include composite gels that are critically reliant on the balance between polymer-polymer and polymer-solvent interactions under various stimuli including changes in temperature, pH, ionic strength, solvent, concentration, pressure, stress, light intensity, and electric or magnetic fields.

Bioactive Materials

As previously stated, in some embodiments, the central tube and/or flow reduction elements of the invention may be adapted to release bioactive materials or bioactive agents that trigger biological satiety signals. In some embodiments, the one or more of the flow reduction elements and/or central tube may be a porous and malleable solid designed to release a signal into the gastrointestinal (GI) tract over time. In some embodiments, nutrient products of digestion are released from the one or more flow reduction elements 200 and/or central tube or elongate member 50 to trigger chemoreceptors within the GI tract to release molecular signals involved in transmitting and/or creating satiety signals.

The description now turns to a consideration of release of bioactive materials from the device in furtherance of reducing appetite or slowing food absorption or intake. The term "bioactive material(s)" refers to any organic, inorganic, or living agent that is biologically active or relevant; the term has been extensively described in U.S. application Ser. No. 11/300,283, and will described here only briefly. For example, a bioactive material may be a protein, a polypeptide, a polysaccharide (e.g. heparin), an oligosaccharide, a mono- or disaccharide, a lipid, an organometallic compound, or an inorganic compound, an antimicrobial agent (including antibacterial and anti-fungal agents), an anti-viral agent, anti-tumor agent, immunogenic agent. It may include a living or senescent cell, a stem cell, a bacterium, a virus, or any part thereof. It may include a biologically active molecule such as a hormone, a growth factor, a growth factor-producing virus, a growth factor inhibitor, a growth factor receptor, an anti-inflammatory agent, an antimetabolite, or a complete or partial functional insense or antisense gene. It may also include a man-made particle or material that carries a biologically relevant or active material. A bioactive material also may be a by-product of digestion or an agent that alters the pH of its surrounding environment.

Bioactive materials also may include drugs such as chemical or biological compounds that can have a therapeutic effect on a biological organism. Bioactive materials also may include precursor materials that exhibit the relevant biological activity after being metabolized, broken-down (e.g. cleaving molecular components), or otherwise processed and modified within the body. Combinations, blends, or other preparations of any of the foregoing examples may be made and still be considered bioactive materials within the intended meaning herein. Aspects of the present invention directed toward bioactive materials may include any or all of the foregoing examples.

Examples of bioactive materials included with the present invention include hormones and other compounds that convey satiety promoting signals. Bioactive materials of the present invention may also include other naturally-occurring or synthesized peptide, protein, and steroid hormones. Bioactive agents further may include anti-tumor agents, antimicrobial agents, such as antibiotics: cephalosporins: aminoglycosides: macrolides: tetracyclines, chemotherapeutic agents, sulfonamides, urinary tract antiseptics, anaerobic infection antibiotics, drugs for tuberculosis, drugs for leprosy, antifungal agents, antiviral agents, chemotherapeutic agents for amebiasis, anti-helminthiasis agents, anti-inflammatory agents, anti-gout agents, centrally acting analgesics, thyroid drugs, including those used in adjunctive therapy, and those used as anti-thyroid agents, viral surface antigens or parts of viruses, bacterial surface antigens or parts of bacteria, surface antigens of parasites causing disease or portions of parasites, immunoglobulins, antitoxins, and antigens that elicit an immune response, such as disease-associated antigens, or bioactive agents such as hormones, enzymes or clotting factors:

Device Features to Accommodate Bioactive Agents for Delivery

The central tube 20 and/or flow reduction elements 200 of the present invention may have bioactive materials adhered to their surface (through dip-coating, spray-coating, sputter-coating and a variety of other techniques known to those of skill in the art) or included in reservoirs or depots accessible to the surface, or may be manufactured so that the materials making up the intestinal insert include and diffuse such bioactive materials. The central tube and/or flow reduction elements of the present invention that diffuse bioactive materials, may be created by a number of different procedures that are referenced in U.S. application Ser. No. 11/300, 283 of Binmoeller, filed on Dec. 15, 2005 and published as U.S. Publication 2006/0178691 on Aug. 10, 2006, including references to U.S. Pat. No. 5,019,400 to Gombotz et al. U.S. Pat. No. 6,685,957 to Bezemer et al. and U.S. Pat. No. 6,685,957.

When a hydrophobic bioactive material, such as a steroid hormone is incorporated by the above-described method, at least one hydrophobic antioxidant may be present. Hydrophobic antioxidants which may be employed include, tocopherols (such as $\alpha$.-tocopherol, $\beta$-tocopherol, $\gamma$-tocopherol, $\delta$-tocopherol, epsilon.-tocopherol, $zeta_1$-tocopherol, $zeta_2$-tocopherol, and eta-tocopherol) and 1-ascorbic acid 6-palmitate. Such hydrophobic antioxidants may retard the degradation of the copolymer and retard the release of the bioactive material.

When a loaded polymer made according to the above-referenced technique includes a hydrophilic bioactive material, the loaded polymer may also include, in addition to a hydrophobic antioxidant, a hydrophobic molecule such as, by way of example, cholesterol, ergosterol, lithocholic acid, cholic acid, dinosterol, betuline, or oleanolic acid, which may serve to retard the release rate of the agent from the copolymer. Such hydrophobic molecules prevent water penetration into the loaded polymer, but do not compromise the degradability of the polymer matrix. Further, such molecules may decrease the polymer matrix diffusion coefficient for the bioactive material to be released and thereby provide for a more sustained release of a bioactive material from the polymer matrix.

Methods of dispersing bioactive materials into polymers and the role of lyophilization to include thermoprotectants have been provided in U.S. application Ser. No. 11/300,283 of Binmoeller, filed on Dec. 15, 2005, which has been incorporated by reference.

Non-limiting examples of polymers that may be used in accordance with the present invention, particularly with regard to accommodating and releasing bioactive agents, include polyurethanes, polyesterurethanes, silicone, fluoropolymers, ethylene vinyl acetate, polyethylene, polypropylene, polycarbonates, trimethylenecarbonate, polyphosphazene, polyhydroxybutyrate, polyhydroxyvalerate, polydioxanone, polyiminocarbonates, polyorthoesters, ethylene vinyl alcohol copolymer, L-polylactide, D,L-polylactide, polyglycolide, polycaprolactone, copolymers of lactide and glycolide, polymethylmethacrylate, poly(n-butyl)methacrylate, polyacrylates, polymethacrylates, elastomers, and mixtures thereof. Representative elastomers that may also be used include, by way of example, a thermoplastic elastomer material available under the trade name "C-FLEX" from Concept Polymer Technologies of Largo, Fla., polyetheramide thermoplastic elastomer, fluoroelastomers, fluorosilicone elastomer, sytrene-butadiene rubber, butadiene-styrene rubber, polyisoprene, neoprene (polychloroprene), ethylene-propylene elastomer, chloro-sulfonated polyethylene elastomer, butyl rubber, polysulfide elastomer, polyacrylate elastomer, nitrile, rubber, polyester, styrene, ethylene, propylene, butadiene and isoprene, polyester thermoplastic elastomer, and mixtures thereof.

One of skill in the art can determine the amount or concentration of bioactive material(s) to include on the surface or within the material of the intestinal inserts of the present invention depending on particular treatment objectives and desired release profiles, as described in U.S. application Ser. No. 11/300,283 of Binmoeller, filed on Dec. 15, 2005, which has been incorporated by reference.

In some embodiments, the intestinal inserts of the present invention, or portions thereof, may include a topcoat or barrier to slow the diffusion or release of bioactive materials. Typically, the barrier should be biocompatible (i.e., its presence does not elicit an adverse response from the body), and may have a thickness ranging from about 50 angstroms to about 20,000 angstroms. In some embodiments the barrier may include a polymer provided over the polymer that diffuses bioactive materials.

In some embodiments, a barrier of the present invention comprises inorganic materials, which have been detailed in U.S. application Ser. No. 11/300,283 of Binmoeller, filed on Dec. 15, 2005, which has been incorporated by reference. Further detailed in that application are several methods that may be used to deposit a barrier over the inserts of the present invention. Nitride barrier coatings, such as, by way of example, titanium nitride, titanium carbonitride, chromium nitride, titanium aluminum nitride, and zirconium nitride may be deposited on the inserts of the present invention at relatively low temperatures by cathodic arc vacuum deposition. Such a method may be chosen where bioactive materials included within an insert of the present invention are temperature-sensitive. Further detailed in that application are methods for producing films of pure metals and alloys.

In some embodiments, it is contemplated that the barrier will contain mostly inorganic material. However, other embodiments may include barriers with a mixture of organic and inorganic materials or barriers of all organic materials. Some organic compounds that may be used in accordance with the present invention include, by way of example, polyacrylonitrile, polyvinylidene chloride, nylon 6-6, perfluoropolymers, polyethylene terephthalate, polyethylene 2,6-napthalene dicarboxylate, and polycarbonate. Generally, the solubility of the drug in the material of the barrier is less than the solubility of the drug in its polymer carrier. Also, generally, the diffusivity of the drug in the material of the barrier is lower than the diffusivity of the drug in its polymer carrier. The some embodiments, the barrier may be biodegradable. Appropriate biodegradable materials that may be used to create a barrier include, by way of example, calcium phosphates such as, by way of example, hydroxyapatite, carbonated hydroxyapatite, tricalcium phosphate, β-tricalcium phosphate, octacalcium phosphate, amorphous calcium phosphate, and calcium orthophosphate. Certain calcium salts such as calcium phosphate (plaster of Paris) may also be used. The biodegradability of the barrier may act as an additional mechanism for controlling drug release from the underlying first layer.

Active Control of Bioactive Material Release

Figure 26:
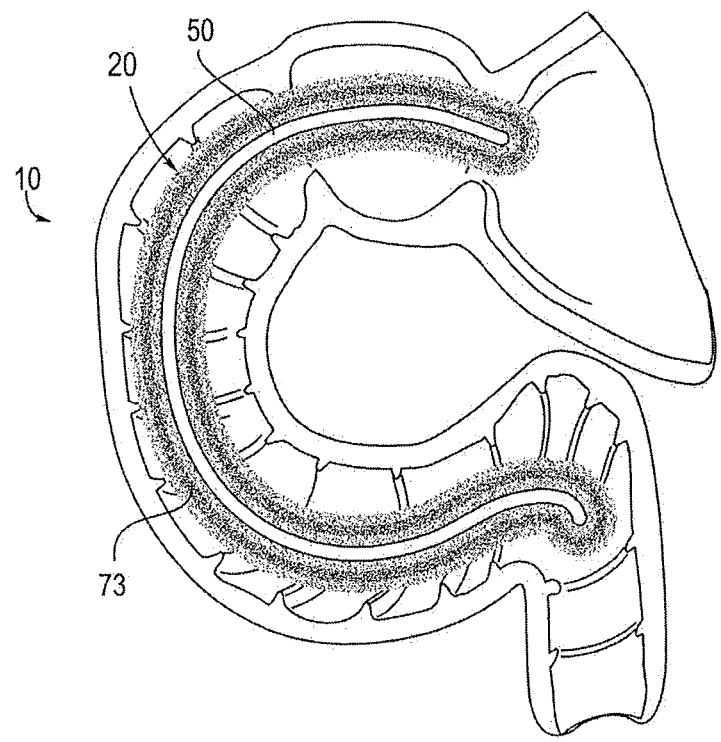
FIG. 26 depicts an embodiment of the insert with bioactive material in reservoirs that passively elute.
Figure 27:
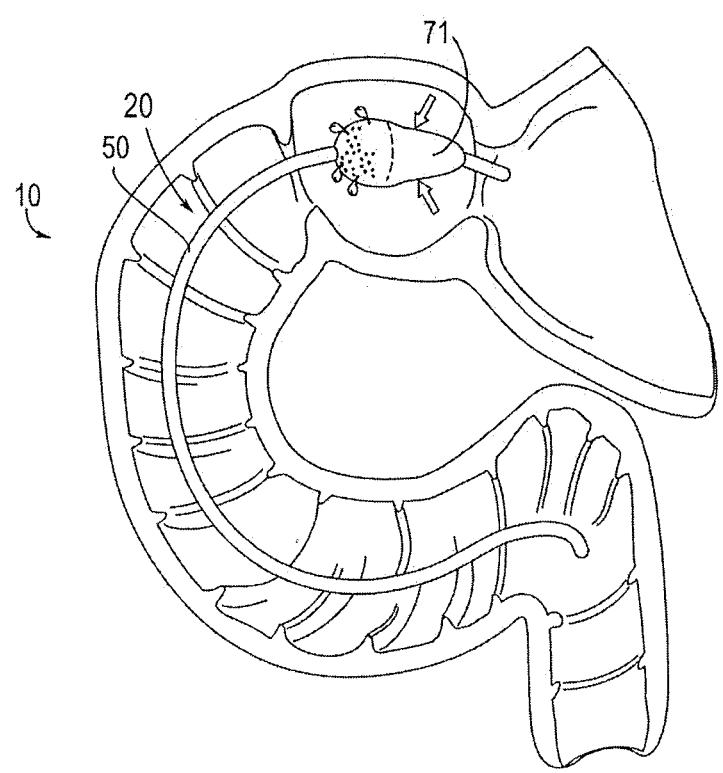
FIG. 27 depicts an embodiment of the insert with a bioactive material-loaded osmotic pump.
Figure 28:
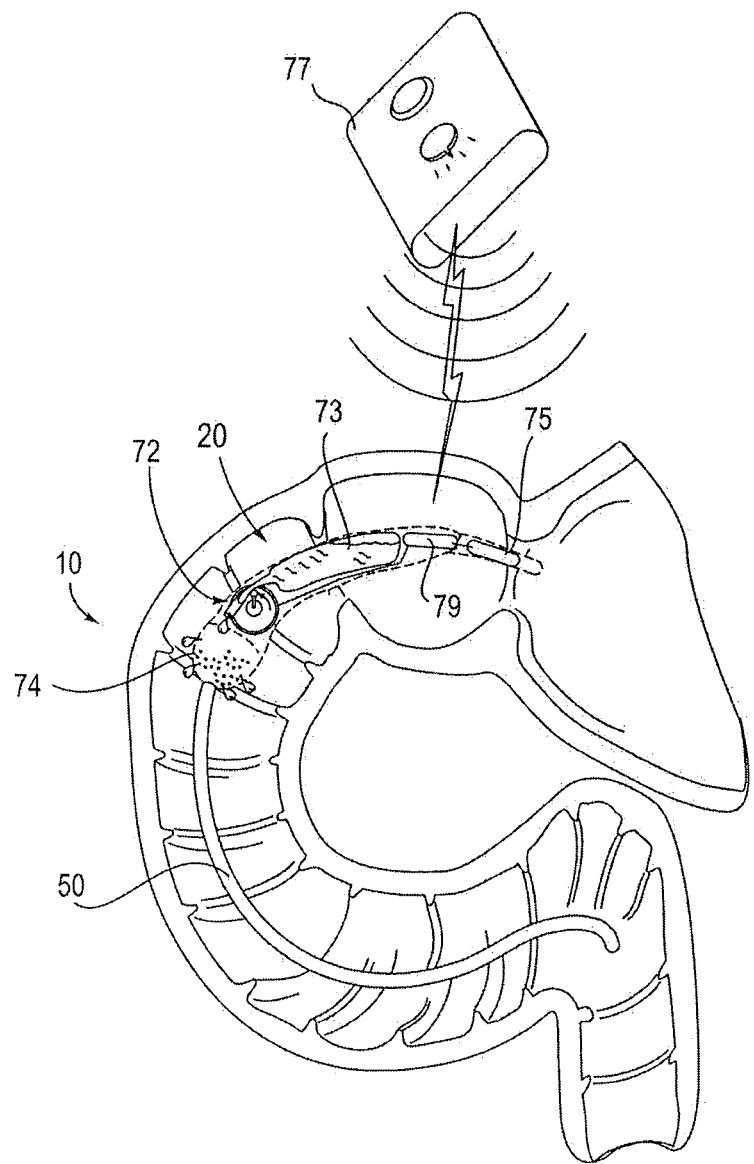
FIG. 28 depicts an embodiment of the insert with a bioactive material loaded reservoir coupled to an electrically driven pump, energy storage unit, and an external control.

Some embodiments of the device and methods provide a more active, i.e., a more controlled, or metered method of delivering bioactive agents, in contrast to the more passive diffusion of drug from surfaces or depots. These approaches are also more amenable to handling the delivery of multiple-drug release. Embodiments of the inventive devise may include a pump to dispense one or more bioactive agents from a reservoir or depot. Pumps may include electrically-driven pumps 72 mechanical pumps, piezo-electric devices that control pores, for example, or pumps may be osmotically-driven pumps 71. The osmotic pump delivery is relatively passive in that it does not require energy input, but it is controllable, predictable, and calibratable. Osmotic pumps typically are driven or urged via pH difference or concentration gradients. Release of bioactive materials may be controlled by external control devices, such as by an electronic signaling device either user-controlled or a programmable pacing/signaling device. Examples of devices that embody these active approaches to the delivery of bioactive materials or agents are described further below, and are depicted in FIGS. 26-28.

There are advantages to a drug delivery site within the intestinal lumen that may, for example advantageously be applied to the delivery of bioactive agents in a broader array than just drugs specific to modulating digestion or appetite. Such other agents may include chemotherapeutic agents, or radioactive particles for anti-cancer therapy. Another type of bioactive material that may benefit from local delivery may include cells, such as stem cells or activated immune cells, for cellular therapy of the intestine. Advantages of the intra-duodenal site of release may include proximity to target sites, taking advantage of specific chemical recovery receptors in the intestine, and minimizing systemic metabolism of drugs that occurs during the passage of the drug through such organs as the liver and kidney that occurs when drugs are delivered intravenously or orally.

In addition to delivering bioactive materials to the small intestine that may reduce food intake, the methods and devices of the present invention may be used to deliver other bioactive materials normally taken orally as well. The release of bioactive materials directly into the small intestine may be advantageous because many bioactive materials, including many drugs that are generally taken orally, are degraded by the harsh conditions of the stomach before they may reach the small intestine to be absorbed. For this reason, many bioactive materials are coated with layers of protective materials. By releasing bioactive materials, including drugs, directly into the small intestine, coatings to protect the bioactive materials may not be required. This lack of required protective coatings may be beneficial for patients because less unnecessary substances are introduced into their systems, and it is further beneficial as a process step reduction and cost reduction measure.

In another aspect of the invention which takes a more active interventional role, embodiments of the device may include an electronic emitter configured to apply an electrical potential to tissue in the stomach or duodenum. This electrical potential will trigger neuron-receptors and/or mechano-receptors, and/or osmo-receptors, and/or chemo receptors to send satiety signals to the brain. Exemplary embodiments of the device such as these are described further below, and depicted in FIG. 29. The role of embodiments of the intestinal insert and methods associated with its use are more generally considered in the context of FIG. 13, as detailed in the following section.

Further Exemplary Embodiments of the Invention

Figure 13:
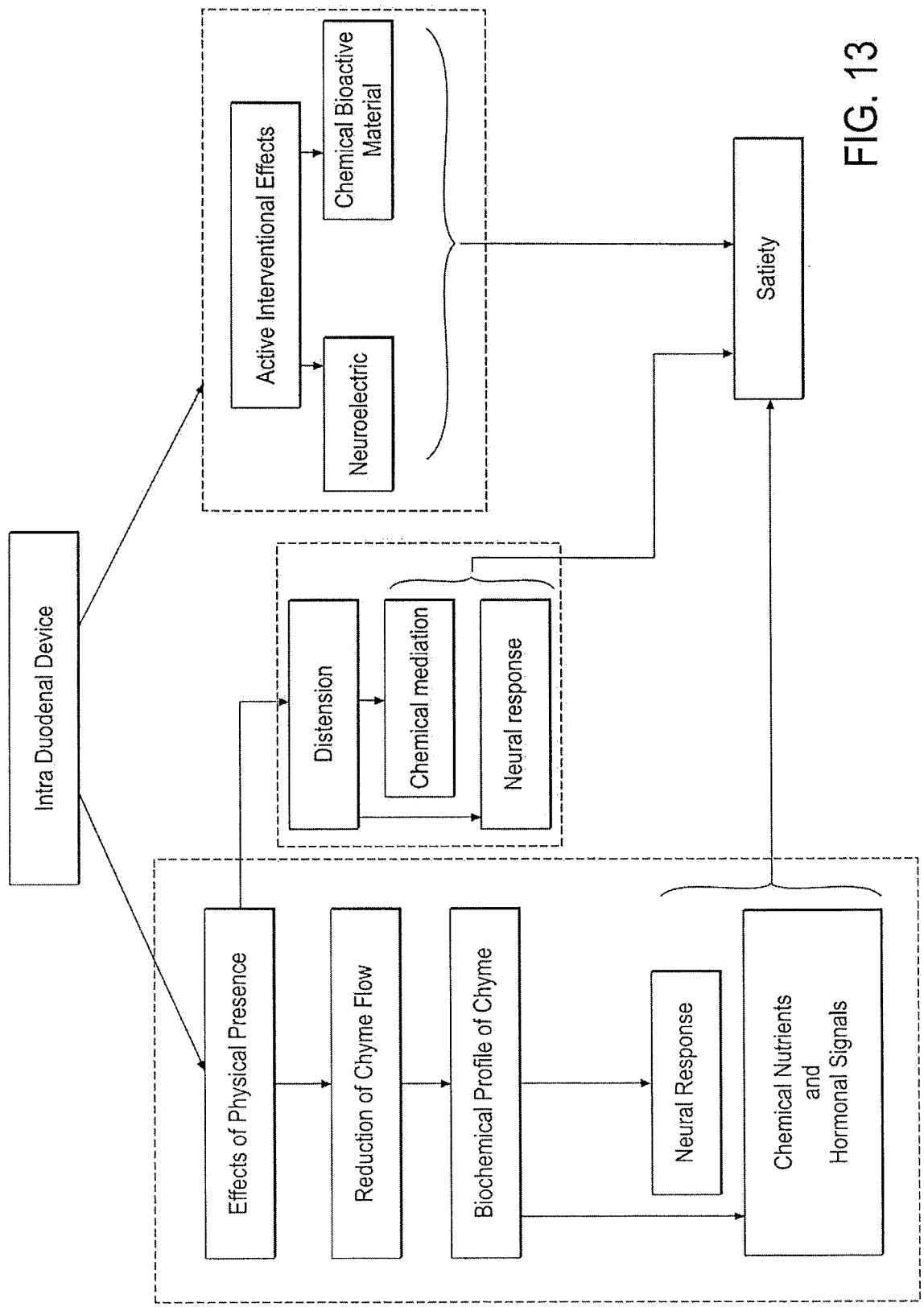
FIG. 13 is a flow diagram depicting the intestinal insert's role in contributing to the generation of one or more signals of satiety.

FIG. 13 is a schematic flow diagram of the various ways in which embodiments of the device engage the physiology of the host subject, and intervene in ways to generate a sense of satiety that ultimately reduces food intake. Embodiments of the inventive device intervene in the physiology of digestion and satiation by two broad approaches, each of which mimic or exploit the natural mechanisms of satiety. Embodiments may engage the physiology of the host subject by (1) their mere physical presence having effects, and/or (2) they may intervene more directly or actively by the direct provision of bioactive agents or direct neural stimulation. FIG. 13 and this associated description are provided as a simplified theoretical framework for understanding the invention; it is not intended to be complete in all detail; various interactions, dotted lines, and blurring of distinctions are omitted for sake of simplicity.

First, the mere physical presence of a device has two main effects, it has distensional effects and, if it has distinct flow reduction elements, it impedes the flow of chyme. Each of these two broad effects is dependent on the dimensions of the device and its flow reduction system, if the latter is present. First, then, the presence of the device distends the duodenum, and such distension may be neurally-sensed or detected, as for example, by stretch-sensitive neurons in the duodenum. Accordingly, any physical dimension, aspect, or feature, such as, by way of example, any of length, width, total volume, overall conformation or topography, density, weight, or surface properties may affect distension, or may be neurally detected in some way. Secondly, with regard to physically impeding the flow of chyme, this impeding process may alter the biochemical profile of digesting chyme, and chemoreceptors in the duodenum sense that profile as being more fully digested. It may also be that there is neural recognition more specifically of longer thyme residency time, as information separate from the altered biochemical profile per se; an effect such as that also then may be related to neural detection of distension. Neuronal pathways are indeed stimulated by distension, and neuroelectric signals and/or neuropeptides and neurotransmitters may be released for local or more distant sites of action. Joining neural feedback are chemical signals, both from the metabolite profile per se, and by the secretion of hormones such as CCK. Neural and chemical responses emanate to the central nervous system and other organs which, in sum, indicate that enough has been eaten, and satiation is achieved. In further response, the central nervous system supports a cessation of eating and digestive processes slow.

Second, with further reference to FIG. 13, embodiments of the device may intervene in a more active manner, beyond that which is provoked by mere physical presence. Embodiments of the device may assertively provide (1) bioactive agents and/or (2) provide electrical stimulation of nerves which then engage the physiology of satiety and digestion in the much the same manner, or through the same physiological pathways described above. In sum, a variety of effects of the presence of the device in the duodenum result in biochemical effects or signals (such as hormonal responses, and/or biochemical profile of metabolites both within the intestine and in the blood stream) and neural activity involving electrical signals, all of which converge physiologically to result in "satiety", with its complement of sensed satiety, sensed or perceived appetite, psychological correlates, and behavioral and habitual responses.

Embodiments of the invention, a small intestinal insert, typically include an elongated member including at least one angled portion and at least one flow reduction element, for slowing the passage of chyme (or, stated in other terms, increasing the residency time of chyme) in the duodenum, although some embodiments of the device do not necessarily include a flow reduction element (as illustrated in FIGS. 26-28), and in some embodiments, the central or elongated member itself may be configured to reduce flow (FIG. 16, for example). These embodiments typically do have one or two angled portions that correspond to angled target portions of the duodenum. The configuration of the angled portions of the insert, including the flow reduction elements, is such that the device resides stably in the duodenum for a period of time. Embodiments of the insert may include adaptations that contribute to the generation of one or more physiological signals of satiety. Embodiments of the insert may include other features, such as the inclusion of biodegradable portions, a neurological stimulator, and one or more releasable reservoirs of bioactive materials that can be actively released by a bioactive material release mechanism.

Residency time of embodiments of the insert within the targeted angled site within the duodenum will vary according to the configuration of the embodiment and according to the particulars of the biodegradable materials that comprise portions of the device. Degradation of the device by biological processes is typically what causes release or unseating, or disengagement of the device from the target site, and elimination of the device through the intestinal tract. It may be understood therefore, that the device may be configured initially to sit or be seated in the targeted angled portion of the small intestine, and then, following a period of residency and through the effects of biodegradation, then configured to be unseated from the target site, and eliminated from the body by way of defecation. Biodegradability is feature of some polymers, and may be included in polymeric portions of any embodiment described herein and/or as illustrated in FIGS. 3-12, and 16-29. Biodegradation is a feature explicitly depicted in the embodiments shown in FIGS. 30 and 31.

Embodiments of the device elicit physiological signals of satiety typically through hormonal or neurological pathways. In some embodiments, the pathways are stimulated by the physical presence of the device, including the sum total of a central member and flow reduction elements, whose collective dimensions, either length, width, or total volume, or surface properties, are such that neuronal elements of the intestine, such as mechanoreceptors or stretch receptors, sense the presence of material which is interpreted as the presence of partially digested food, and therefore stimulate neuronal messages to the central nervous system that are interpreted as food satiation. In other embodiments, the satiety signal may be hormonal. Flow reduction elements slow the passage of chyme being processed in the duodenum, the biochemical profile of the food breakdown products is altered, and chemoreceptors in the duodenum respond to the altered biochemical profile in a manner that conveys satiety to the central nervous system and other portions of the digestive system.

In still other embodiments, the device includes reservoirs of bioactive materials that may be released, either by passive or active mechanisms. In the embodiments, the satiety signals are provided directly by the device, not by the endocrine pathways of the insert's host. Embodiments of the device may include material reservoirs of any type, including, for example, drug coatings that elute passively, or in concert with degradation of a host coating material, and some embodiments include reservoirs that are coupled with pumps. Such pumps may be mechanical, harnessing for example, biological energy conveyed by peristalsis, or electrical energy, or mechanical energy. Some embodiments may include osmotic pumps, which do not require input of electrical energy, but instead tap into the stored energy of osmotic gradients. Embodiments that are dependent on electrical energy for release by a pump typically include an energy storage device, such as a battery or a capacitor. Some of the powered embodiments include, as part of a larger system, a remote stimulator that can control the action of the pump. In some embodiments, the device may provide direct neural stimulation, through electrodes that stimulate local nerves in the duodenum, which convey a sensation of satiety to the central nervous system. As with pumps, devices that include neural stimulation features, may also include energy storage devices and external on/off or variable power control devices that communicate either by direct wired connection or wirelessly, as for example through radiofrequency signals.

Figure 14:
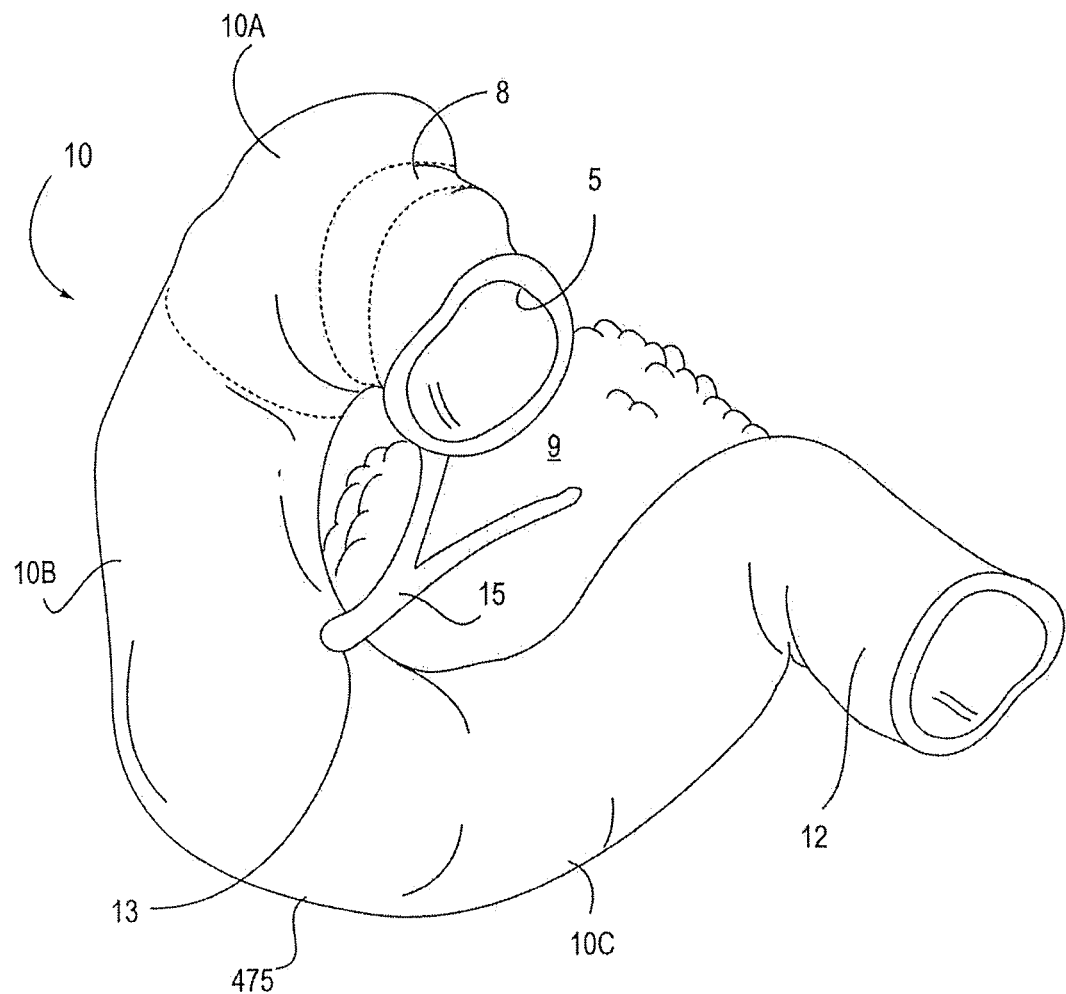
FIG. 14 is perspective view of the duodenum.
Figure 15:
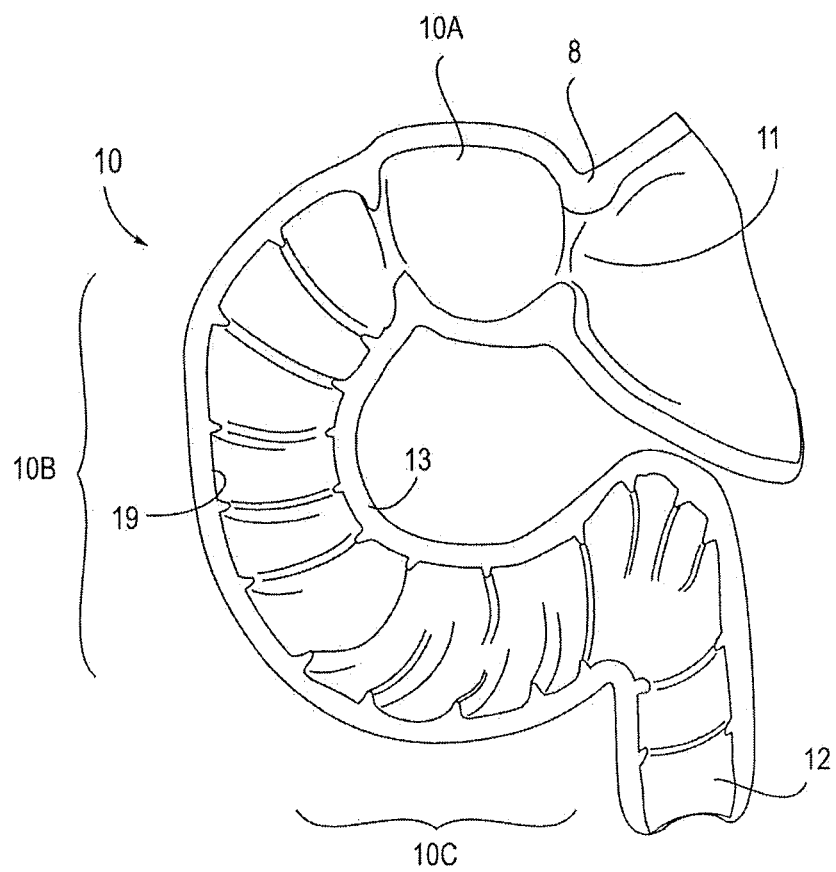
FIG. 15 depicts a side view of the duodenum, showing the folds of rugae that form the periphery of the inner space within which embodiments of the insert device are positioned.

FIG. 14 provides a view of a portion of the human gastrointestinal tract that focuses on the duodenum of the small intestine 10, starting at the antrum-pyloric juncture 5, and extending to the entrance of the jejunum 12. Shown are the ampulla of Vater 13, the site of the entrance of the hepatopancreatic duct 15, which is formed by the union of the pancreatic duct (from the pancreas 9) and the common bile duct from the liver. The pylorus 8 controls the discharge of contents of the stomach through a sphincter muscle, the pyloric valve 11, which allows the pylorus 8 to open wide enough to pass sufficiently-digested stomach contents. These gastric contents, after passing into the duodenum 10, continue into the jejunum 12 and on into the ileum. The duodenum 10, jejunum 12 and ileum make up what is known as the small intestine, however the individual portions of the alimentary canal are also commonly referred to as the small intestine. In the context of this invention the small intestine can refer to all or part of the duodenum, jejunum and/or ileum. FIG. 15 provides a flattened planar view of the duodenum 10, including the rugae 19, or inner-folding lining portion of the duodenum that form the periphery of the inner space within which embodiments of the insert device are positioned. Also depicted are the pylorus 8, the pyloric valve 11, the duodenal bulb 10A, the vertical duodenum 10B, and the horizontal duodenum 10C, the ampulla of Vater 13, and the initial portion of the jejunum 12. This figure provides a visual background for FIGS. 16-29 that follow, each of which depicts an embodiment of the inventive inserted device seated within the targeted site of the duodenum.

Figure 16A:
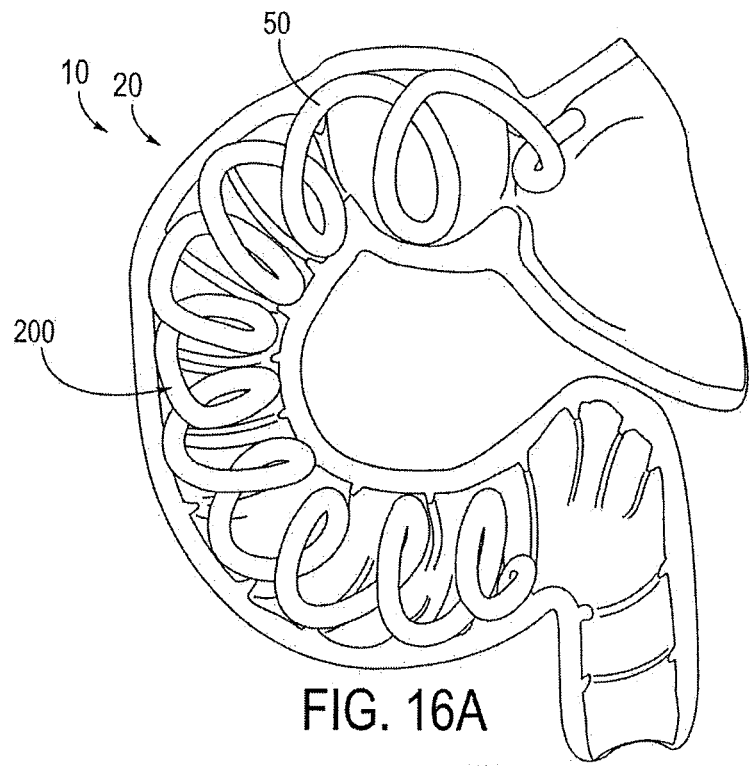
FIGS. 16A-16B depict an embodiment of the insert with flow reduction elements in the form of a simple coil.
Figure 16B:
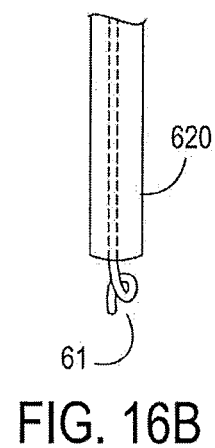

FIG. 16A depicts an embodiment of the insert 20 with a central tube or member 50 in the form of a simple coil like a telephone cord; in this embodiment the flow reduction elements 200A may be understood as the individual coiled elements or segments of the extended central member 50. FIG. 16B shows a detail of a proximal or distal end portion of the device that takes the form of a pig-tail 61, as it would emerge from a device deployment tube 620. Pig-tail end portion embodiments may provide utility and advantage during deployment, as well as a stabilizing and non-irritating end-point when the insert is seated in the target site.

Figure 17A:
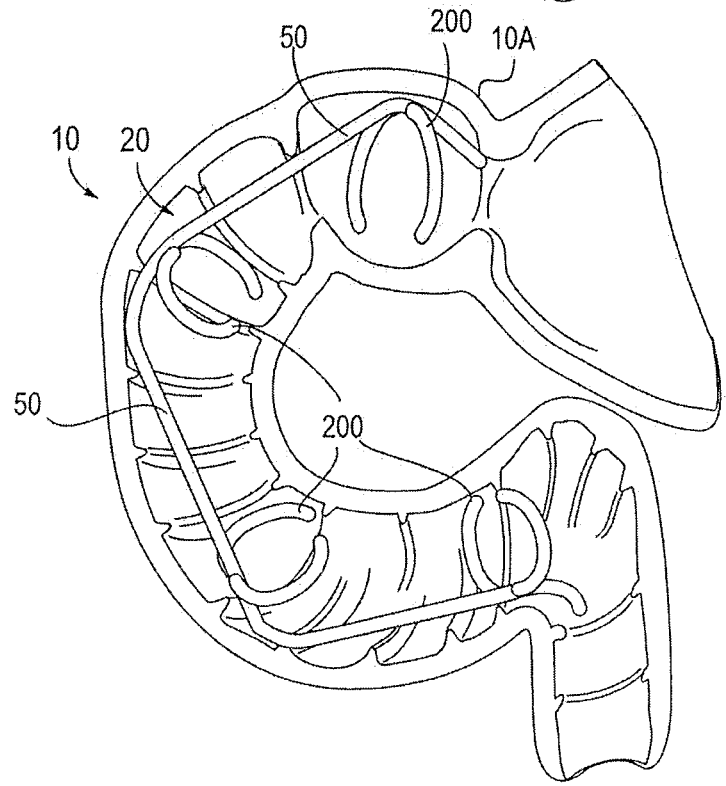
FIGS. 17A-17B depict an embodiment of the insert with flow reduction elements in the form of a spine with ribs.
Figure 17B:
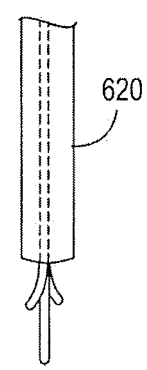

FIG. 17A depicts an embodiment of the insert 20 with a central tube or member 50 in the form of a C-shaped spine, similar to the embodiment depicted in FIGS. 3 and 9, with flow reduction elements 200 in the form of ribs attached to the spine. FIG. 17B shows the central member 50 and tips of ribs 200 emerging from a deployment tube 620. Some embodiments of the rib-formed flow reduction elements 200 may be spring-like and outwardly biased, the elements reducing flow by their presence, but also, and advantageously, stimulating the wall of the duodenum 10, thereby contributing to the generation of a satiety signal, and further, contributing to stabilization of the insert as it resides within the targeted and angled site of the duodenum. In the latter regard, the duodenal bulb portion 10A bulges out to a wider radius than the more distal portion of the duodenum, and thus, an expansive element in this site provides a particularly effective stabilization site.

Figure 18:
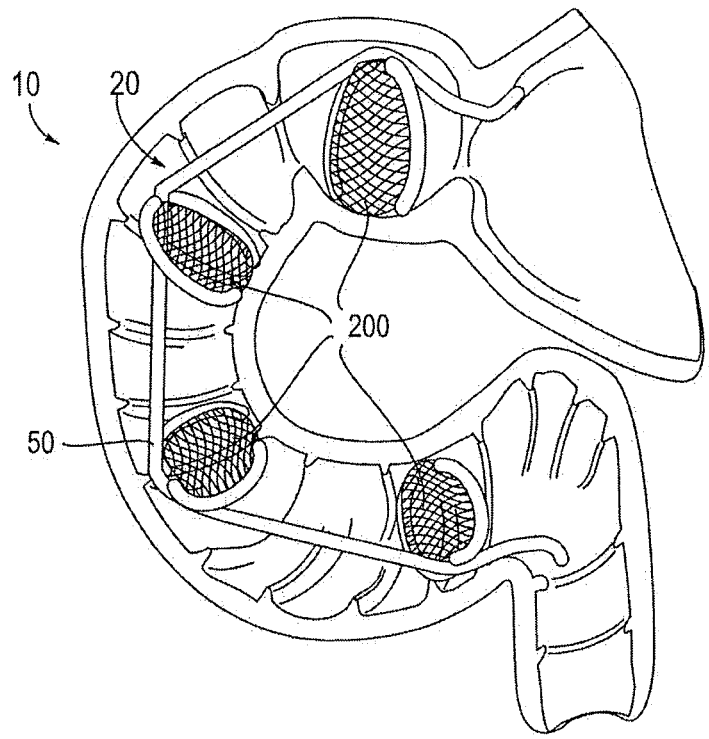
FIG. 18 depicts an embodiment of the insert with flow reduction elements in the form of a spine with nets.

FIG. 18 depicts an embodiment of the insert 20 with flow reduction elements in the form of a spine with nets. This embodiment may be considered similar to that shown in FIG. 17, but with a net, filter, or mesh deployed between expandable ribs. The expandable ribs provide benefits as described above; the netting provides leverage in terms of reducing the flow of chyme being processed through the duodenum 10. By use of mesh of varying pore size in the flow reduction elements 200, the device may be provided in variations that slow the flow rate to varying degree. Further, the mesh elements may be formed of materials of varying properties, such as varied hydrophilicity or hydrophobicity, which may have effects on chyme flow rate. Further still, the mesh may provide a site advantageous by virtue of its high surface area for the adsorption of bioactive materials, which may then passively elute or desorb during the period that the insert 20 resides in the duodenum.

Figure 19:
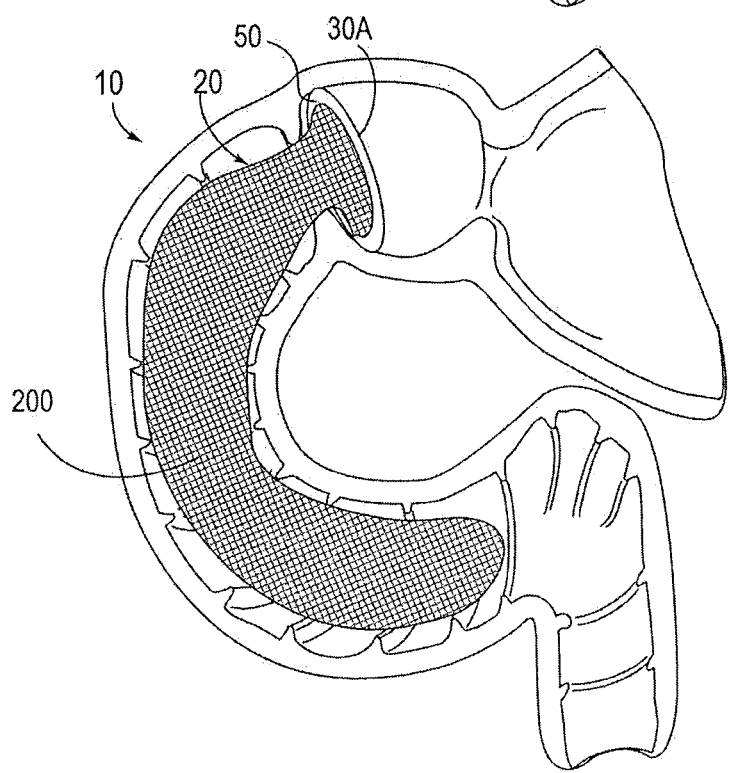
FIG. 19 depicts an embodiment of the insert with flow reduction elements in the form of a sleeve.

FIG. 19 depicts an embodiment of the insert 20 with flow reduction elements in the form of a distally-closed sleeve that is secured by a proximal portion 30A in the form of a proximally-open ring-like end cap. The sleeve may have pores of various dimensions, providing leakage of various degrees, and generally provide the features ascribed to the nets of the embodiment depicted in FIG. 18.

Figure 20A:
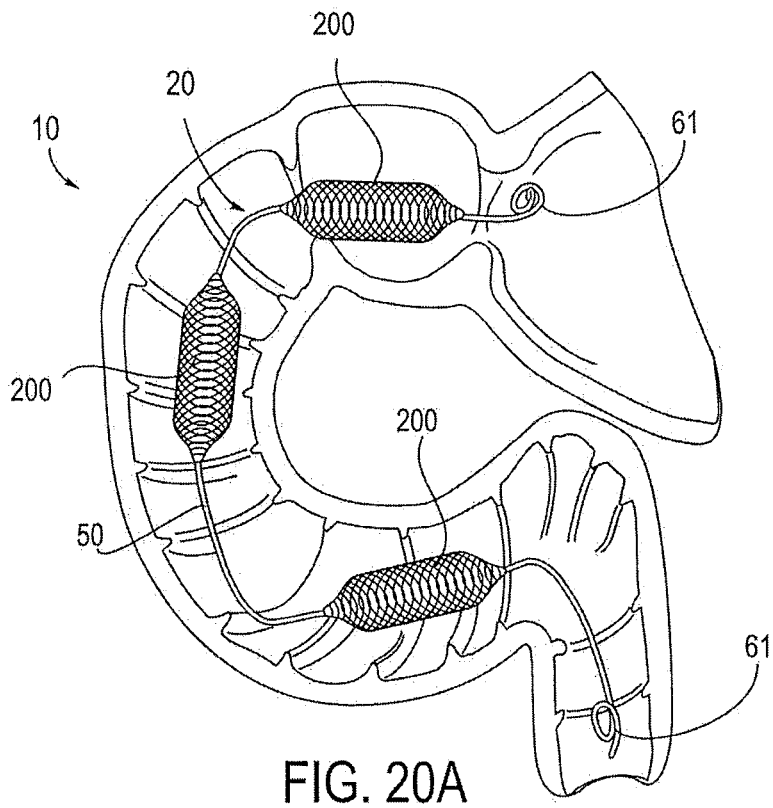
FIGS. 20A-20B depict an embodiment of the insert with flow reduction elements in the form of closed mesh baskets, and further showing pig-tail proximal and distal ends.
Figure 20B:
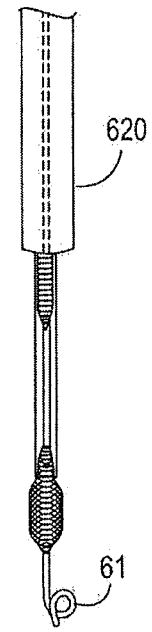

FIG. 20A depicts an embodiment of the insert 20 with flow reduction elements 200 in the form of closed mesh baskets along a central member 50 and contiguous with it, and further showing pig-tail proximal and distal ends 61. FIG. 20B shows the device emerging from a deployment tube 620, and expanding on emergence. Embodiments of the mesh baskets are flexible and expandable, the mesh may be of varying dimension and composition. Typically, the basket portions themselves do not form angles, but the interconnecting central portion 50 may form and resiliently hold predetermined angles. The composition of the baskets and the central portion may be identical and continuous, or the compositions may vary from each other. The interconnecting central portion 50, in particular, may further have shape-memory features, as provided either by shape memory alloys or shape memory polymers. The polymeric materials comprising the baskets 200 and/or the central member 50, whether resiliently shape-holding, or shape-memory capable, may further be biodegradable.

Figure 21:
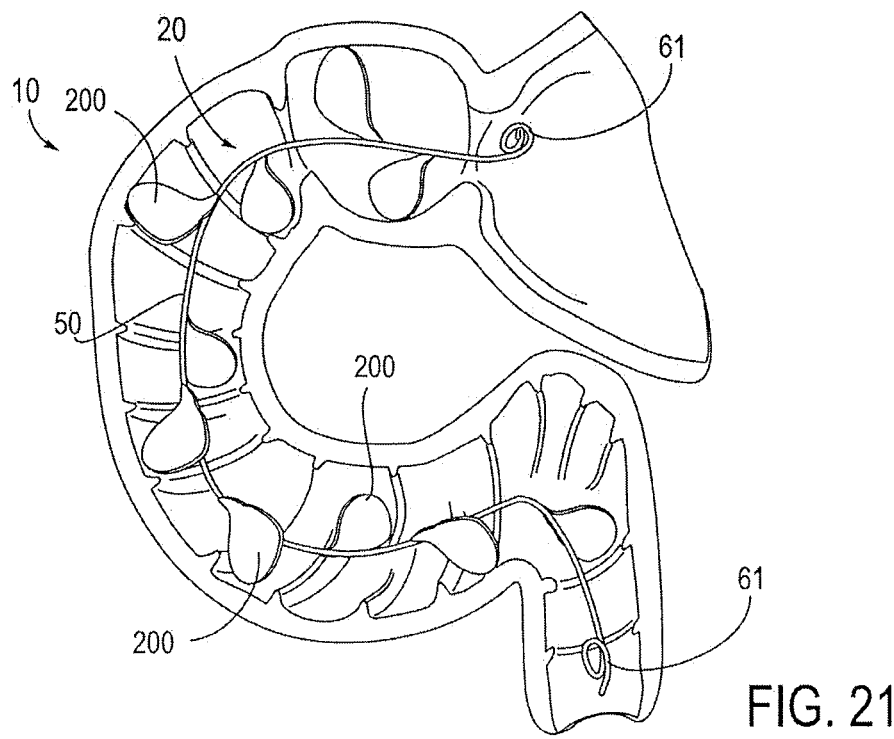
FIG. 21 depicts an embodiment of the insert with flow reduction elements in the form of centrally-mounted outwardly-extending baffles, and further showing pig-tail proximal and distal ends.

FIG. 21 depicts an embodiment of the insert 20 with flow reduction elements 200 in the form of centrally-mounted outwardly-extending baffles, and further showing pig-tail proximal and distal ends 61. The baffles are mounted at spatial intervals on a central member 50, that may include angled portions that are maintained by resiliently-shaped or memory-shaped materials, as described in the context of the embodiment shown in FIG. 20.

Figure 22:
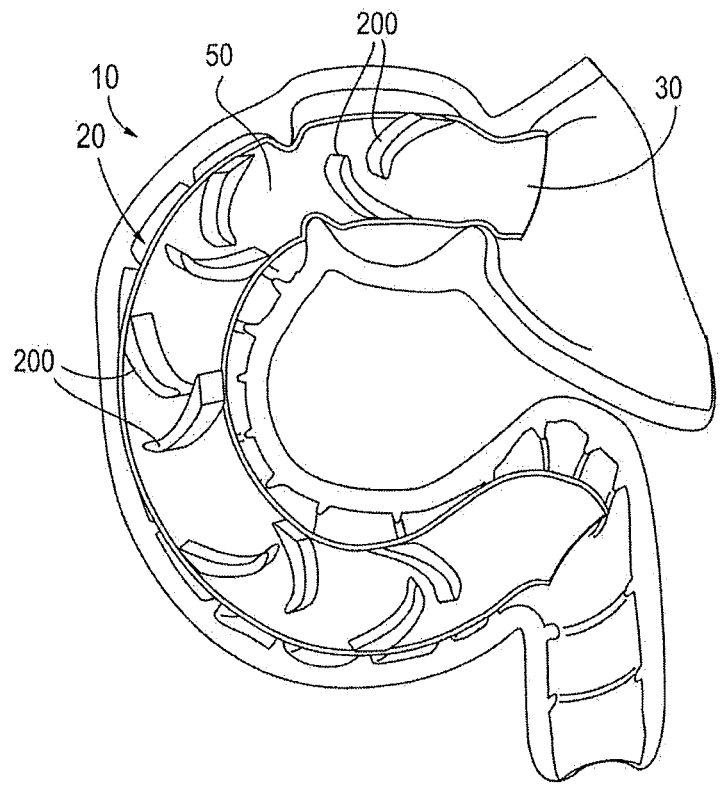
FIG. 22 depicts an embodiment of the insert with flow reduction elements in the form of peripherally-mounted inwardly-extending baffles, and further showing pig-tail proximal and distal ends.

FIG. 22 depicts an embodiment of the insert 20 with flow reduction elements 200 in the form of peripherally-mounted inwardly-extending baffles, and further showing pig-tail proximal and distal ends 61. The baffles are mounted at spatial intervals on a hollow central member 50 that may include angled or curved portions that are maintained by resiliently-shaped or memory-shaped materials, as described in the context of the embodiment shown in FIGS. 20 and 21. This embodiment differs generally from many others depicted by virtue of it hollow body aspect. The device 20 is open both at its proximal portion 30 and distal portion 40. This hollow form may confer some particular advantages with regard to contributing to the generation of satiety signals. The form of the device is space-filling within the duodenum 10, and accordingly may be particularly well suited for the stimulation of mechanically-responsive or stretch-responsive nerves within the duodenal wall, the stimulation of such nerves generally providing a sensation of satiety. The device 20 in this form may also have a force distribution advantage over those with a more centrally-disposed central member 50, as seen in most other depicted embodiments. Further, the configuration of the surface of the device 20 may vary; it may, for example be solid or housing-like, it substantially housing-like, but with holes or openings (not shown), or it may be cage-like or mesh-like (not shown). Each of these forms may have particular advantages. Further, with a more substantial physical presence, a housing-like device provides a physical platform for attachment or mounting of drug reservoirs, as well as pumps and circuitry, as depicted in another embodiment in FIGS. 27 and 28. Further, such a housing-like form may provide an appropriate mounting for neurally-stimulating electrodes, as depicted in an embodiment shown in FIG. 29. This particular embodiment may be understood as being particularly amenable to capturing kinetic energy from the body in the form of peristaltic movement with the baffles, particularly when they have a spring bias. Such capturing of energy may have benefits with regard to slowing the flow of chyme, while reducing likelihood of clogging or creating pockets of chyme that become isolated and stalled with regard to the main flow.

Figure 23:
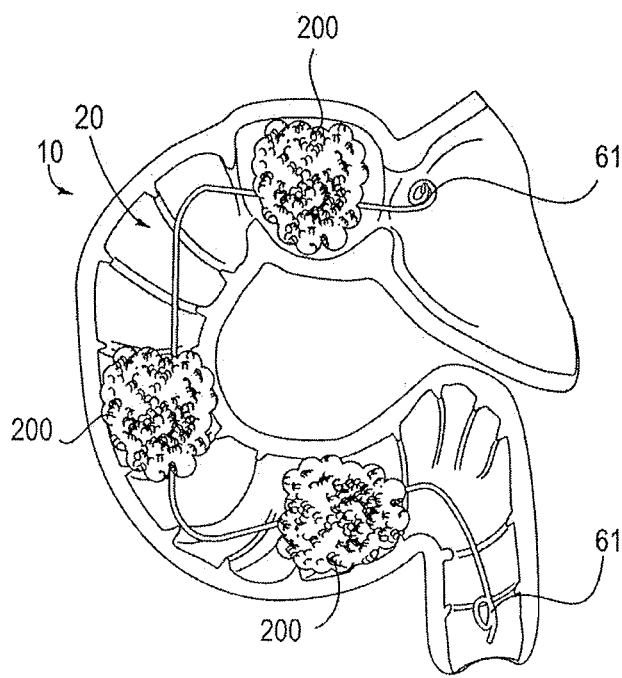
FIG. 23 depicts an embodiment of the insert with flow reduction elements in the form of a foam-like bodies, and further showing pig-tail proximal and distal ends.

FIG. 23 depicts an embodiment of the insert 20 with flow reduction elements 200 in the form of a foam-like bodies, and further showing pig-tail proximal and distal ends 61. This embodiment, in broad aspect, is similar to the embodiment shown in FIG. 6. Foam-like flow reduction elements 200 are compressible and expandable, and are thereby amenable to deployment into a target zone through narrow tubes or scopes. The foam-like materials may be of a closed-cell form or an open-cell form, or they may be hydrogels. Such foam-like materials serve the flow reduction function well because they are bulky, compliant, and tend to be space-filling. They also provide a high amount of surface area, which is advantageous for adsorption of bioactive agents, as provided by embodiments of the invention, that may then be passively desorbed during the residency period within the duodenum. Such foam or sponge-like materials may also be wholly or partially biodegradable. The biodegradability generally serves the purpose of providing for a limited residency time, as well as being a way in which to disperse bioactive agents incorporated or adsorbed onto the material.

Figure 24:
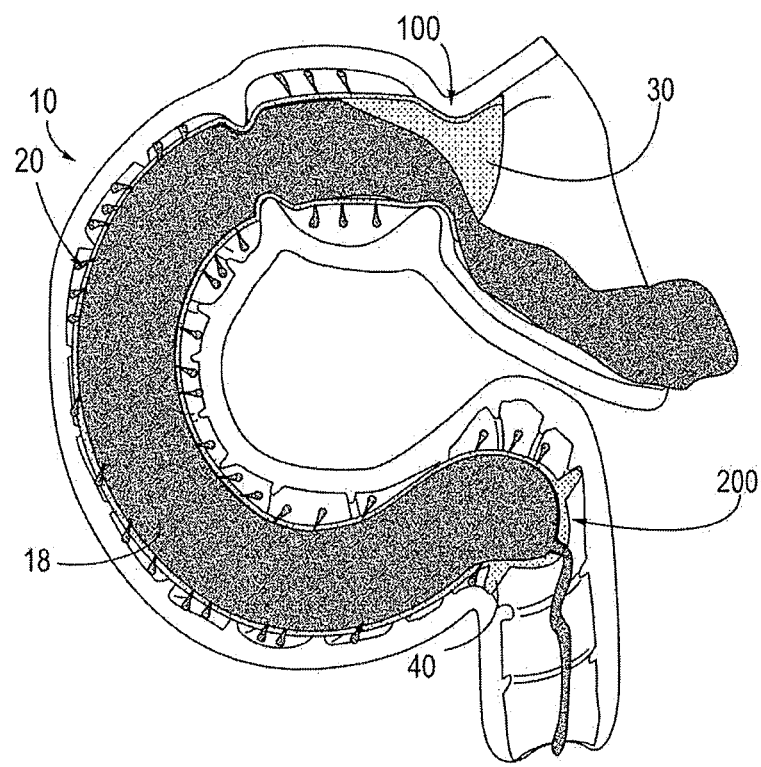
FIG. 24 depicts an embodiment of the insert with flow reduction elements in the form of a porous nutrient weeping stent.

FIG. 24 depicts an embodiment of the insert 20 with a flow reduction element 200 in the form of a porous nutrient-weeping stent, open both at the proximal end 30 and the distal end 40. This embodiment differs generally from that depicted in FIG. 19 for having greater integrity in form; in contrast, the embodiment of FIG. 19 is referred to an open sleeve, and has no particular structural form. The nutrient-weeping stent embodiment depicted here has structural integrity and is more assertively space-filling. The material typically takes the form of a mesh, as with other types of intraluminal stents, and may be formed from polymeric and/or metal strands. The mesh is typically open enough to provide a weeping of liquefied nutrient-rich portions of processing chyme 18, while maintaining the bulk flow of chyme within the channel enclosed by the stent.

Figure 25:
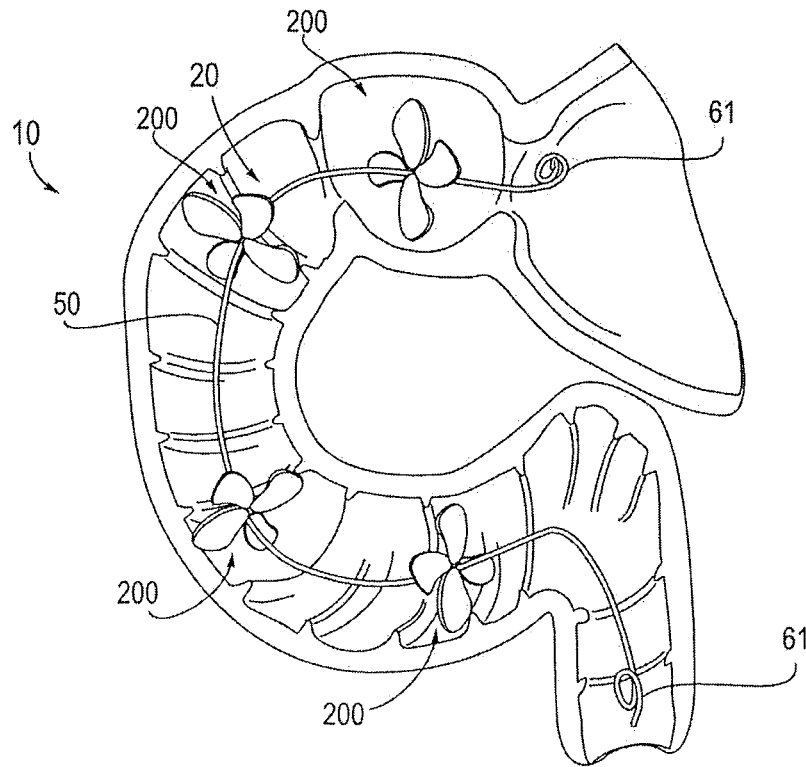
FIG. 25 depicts an embodiment of the insert with flow reduction elements in the form of a centrally-mounted fans, and further showing pig-tail proximal and distal ends.

FIG. 25 depicts an embodiment of the insert 20 with flow reduction elements 200 in the form of a centrally-mounted fans or blades, mounted at spatial intervals on a central member 50, and further showing pig-tail proximal and distal ends 61. Such fan blades 200 may be rotatable, with variable degrees of resistance to rotation, including minimal resistance. To the extent that such flow reduction embodiments 200 do rotate in accordance with the flow of processing chyme, such movement may be beneficial in similar ways to those described in the embodiment depicted in FIG. 22, in that mixing of chyme may be a useful process as an adjunct to reducing flow rate.

FIG. 26 depicts an embodiment of the insert 20 with bioactive material in reservoirs or depots, or layered, or adsorbed, or incorporated on the central- or elongated member 50, from which the bioactive agent may passively elute into the duodenum 10. This embodiment emphasizes the bioactive material or agent delivery aspect of the devise, and it is shown without any particularly formed flow reduction element other than its own physical dimension, however, it should be understood that a drug eluting central member 50 such as this may be combined with any of the various flow reduction elements 200 depicted in other figures.

FIG. 27 depicts an embodiment of the insert 20 with a bioactive material-loaded osmotic pump 71, as supported by central or elongate member 50. Osmotic pumps are well known in the art, as provided, for example, by Alza Corporation (Cupertino, Calif.). The actuation of an osmotic pump may occur in various ways; for example, water driven by a chemical potential crosses an osmotic membrane and enters a salt chamber. The increased volume in the salt chamber forces an expansion membrane to deflect into a drug reservoir. As the expansion membrane pushes into the reservoir, the drug is dispensed via one or more outlet ports.

FIG. 28 depicts an embodiment of the insert 20 with a bioactive material loaded reservoir 73 coupled to an electrically driven pump 72, energy storage and dispensing unit 75, all such components being supported by central or elongate member 50, as well as external control 77. As in FIGS. 26 and 27, the presently depicted embodiment emphasizes the delivery of a bioactive agent or material to the targeted duodenal site. Any of these embodiments could include more than one drug. The difference between this bioactive agent dispensing embodiment and those of FIGS. 26 and 27 is that they are relatively passive, running on a predetermined time course as determined by the particulars of bioactive agent release mechanism. In the embodiment depicted in FIG. 28, however, the release of the bioactive material is under active control of a pump, and the pump may be further under the control of an external control that communicates to the pump either by an implanted wire, or, as depicted here, by wireless communication, as for example by radiofrequency transmission. A device may include more than one such unit, or a single unit may include more than one reservoir and pump, thus more than one bioactive agent may be delivered independently from a single device 20.

Figure 29:
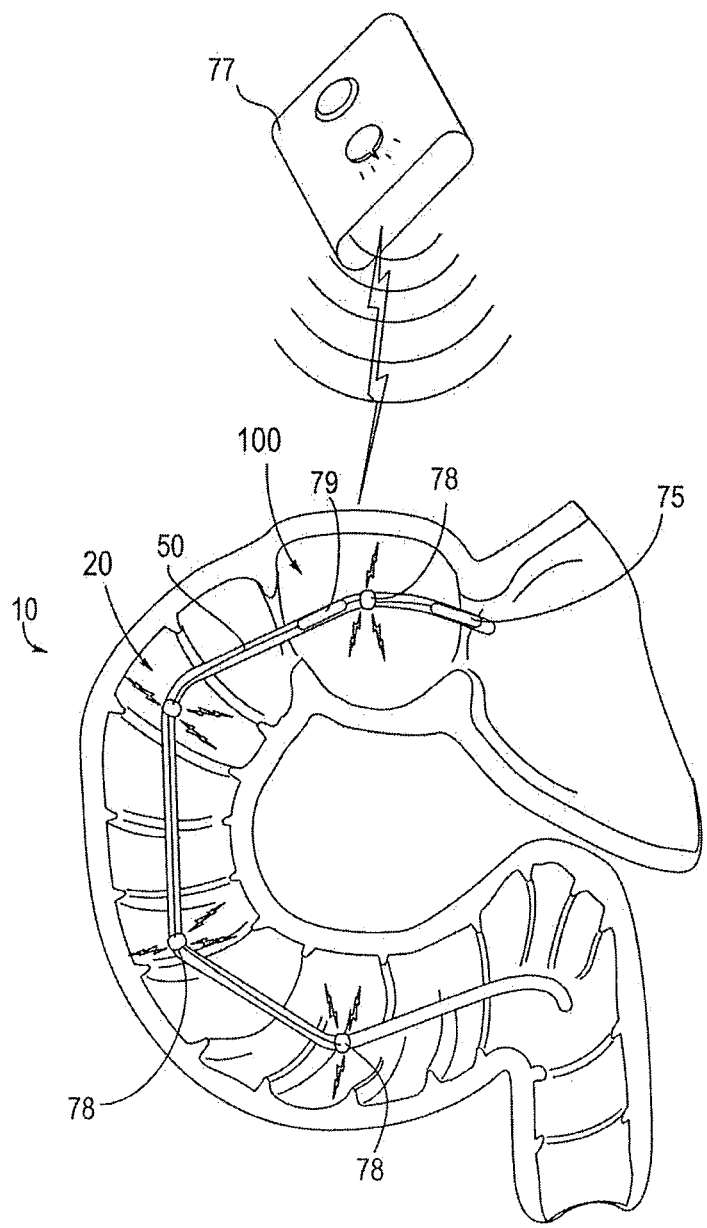
FIG. 29 depicts an embodiment of the insert with electrodes for local neurostimulation, an energy storage unit, and an external control.

FIG. 29 depicts an embodiment of the inventive insert 20 with electrodes 78 for local neurostimulation, an energy storage and delivery unit 75, such as a battery or capacitor, and an external controller 77, all such components being supported either directly or indirectly by the central or elongate member 50. This embodiment is illustrated in such a way so as to focus on neuronal stimulation, but as explained above in reference to drug-eluting devices, the neural stimulatory features of the device may be combined with any of the various flow reduction elements 200. In the present embodiment, the electrodes may be advantageously positioned at sites where nerves are known to reside. Electrodes may target more than one nerve to stimulate, or may target a nerve at more than one point.

FIG. 30 depicts an embodiment of the central member 50 of an insert 20 that includes biodegradable elements and shape memory elements. FIG. 30A shows the central member in an intact configuration with angles α and β apparent; FIG. 30B shows the central member after biodegradation has begun. At a later point, the central member will deteriorate further, lose its integrity and conformation, and the angles α and β will disappear as the defining arms of the C-shape device disappear. As such, this represents an embodiments of device that is configured first to sit within a targeted site in the intestine, and then following residency and a period of biodegradation, the device is configured to become unseated from the target site, such unseating due to the loss of the initial conforming correspondence to the target site. In the exemplary embodiment depicted here, an insert device 20 is formed from a combination of curved shape-memory alloy portions 22 and relatively straight biodegradable polymer portions. The metal portions 22 and polymer portions 24 are joined together segmentally to create an insert of full dimension and with a complete an angle or curve as desired, such as angles of radius α and radius β depicted in FIG. 9. The metal portions have expanded portions at either end to provide a more substantial joining surface, and to protect the host subject from injury or irritation from sharps, as the metal elements are loosed upon biological degradation of the member 20 as a whole. Metal and polymer portions may be joined together in other ways to complete an angled device, as would be familiar to those skilled in the art.

FIG. 31 depicts an embodiment of the central member 50 of an insert that includes a biodegradable polymeric material; biodegradable polymers have been described extensively, above. FIG. 31A shows the central member in an intact configuration; FIG. 31B shows the central member after biodegradation has begun. At a later point, the central member 50 will further disintegrate, and angles of radius α and radius β will no longer hold their form. In some embodiments, the polymeric material may be capable of resiliently holding an angle, such as angles of radius α and radius β depicted in FIG. 9, and in other embodiments, the polymer may be of a type capable of holding a shape memory, as described above.

Terms and Conventions

Unless defined otherwise, all technical terms used herein have the same meanings as commonly understood by one of ordinary skill in the art to which this invention belongs. Various conventions and terms have also been described in the related U.S. application Ser. No. 11/300,283. Specific methods, devices, and materials are described in this application, but any methods and materials similar or equivalent to those described herein can be used in the practice of the present invention.

While embodiments of the inventive device and method have been described in some detail and by way of exemplary illustrations, such illustration is for purposes of clarity of understanding only, and is not intended to be limiting. Various terms have been used in the description to convey an understanding of the invention; it will be understood that the meaning of these various terms extends to common linguistic or grammatical variations or forms thereof. It will also be understood that when terminology referring to devices, equipment, or drugs has used trade names, brand names, or common names, that these names are provided as contemporary examples, and the invention is not limited by such literal scope. Terminology that is introduced at a later date that may be reasonably understood as a derivative of a contemporary term or designating of a subset of objects embraced by a contemporary term will be understood as having been described by the now contemporary terminology. Further, while some theoretical considerations have been advanced in furtherance of providing an understanding, for example, of the various ways that embodiments of the invention engage the physiology of satiety, the claims to the invention are not bound by such theory. Moreover, any one or more features of any embodiment of the invention can be combined with any one or more other features of any other embodiment of the invention, without departing from the scope of the invention. Still further, it should be understood that the invention is not limited to the embodiments that have been set forth for purposes of exemplification, but is to be defined only by a fair reading of claims that are appended to the patent application, including the full range of equivalency to which each element thereof is entitled.

What is claimed is:

1. A gastrointestinal insert, comprising:
   an elongated member configured to be placed in a patient's duodenum, wherein the elongated member has a proximal end, a distal end, and a longitudinal axis extending from the proximal end to the distal end;
   a plurality of porous flow reduction elements comprising mesh baskets along the elongated member, the mesh baskets comprising a shape-memory material and expandable from a stowed configuration to a deployed substantially spherical configuration; and
   an anchor connected to the proximal end of the elongated member, wherein the anchor is configured to be placed in a stomach to anchor the mesh baskets in the duodenum.

2. The gastrointestinal insert of claim 1, wherein the mesh baskets in the substantially spherical configuration define an enclosed space.

3. The gastrointestinal insert of claim 1, wherein the longitudinal axis is curved into a curved shape that mimics a portion of a small intestine.

4. The gastrointestinal insert of claim 3, wherein the elongated member is configured to bend and return to the curved shape after insertion into the duodenum.

5. The gastrointestinal insert of claim 1, wherein the mesh baskets in the deployed substantially spherical configuration are configured to reduce the flow rate of chyme in a patient's small intestine.

6. The gastrointestinal intestinal insert of claim 1, wherein the mesh baskets in the deployed substantially spherical configuration encircle the elongated member.

7. The gastrointestinal insert of claim 1, wherein the elongated member is solid.

8. The gastrointestinal insert of claim 1, wherein the mesh baskets are contiguous with the elongated member.

9. The gastrointestinal insert of claim 1, wherein the mesh baskets in the deployed substantially spherical configuration are concentrically arranged about the elongated member.

10. The gastrointestinal insert of claim 1, wherein the shape memory material is a polymer.

11. The gastrointestinal insert of claim 1, wherein the shape memory material is a metal alloy.

12. The gastrointestinal insert of claim 1, wherein the insert is configured to generate a hormonal signal of satiety when the mesh baskets are in the duodenum.

13. The gastrointestinal insert of claim 1, wherein the anchor is configured to restrict distal migration of the elongated member.

14. The gastrointestinal insert of claim 1, wherein the elongated member comprises a shape memory material.

\* \* \* \* \*